United States Patent
Pinney et al.

(10) Patent No.: US 9,105,142 B2
(45) Date of Patent: Aug. 11, 2015

(54) RANDOM ACCESS AND RANDOM LOAD DISPENSING UNIT

(75) Inventors: Linda J. Pinney, Del Mar, CA (US); John A. Beane, San Diego, CA (US); Angus R. Colson, Jamul, CA (US); David R. Williams, Rainbow, CA (US); Keith Kopitzke, Fallbrook, CA (US); Keith W. Reynolds, Cardiff By The Sea, CA (US); Erik Howard Barnes, Solana Beach, CA (US)

(73) Assignee: Asteres, Inc., San Diego, CA (US)

( * ) Notice: Subject to any disclaimer, the term of this patent is extended or adjusted under 35 U.S.C. 154(b) by 933 days.

(21) Appl. No.: 12/949,939

(22) Filed: Nov. 19, 2010

(65) Prior Publication Data

US 2011/0137455 A1    Jun. 9, 2011

Related U.S. Application Data

(60) Continuation of application No. 11/520,928, filed on Sep. 13, 2006, now Pat. No. 7,857,161, which is a division of application No. 10/880,269, filed on Jun. 29, 2004, now abandoned, which is a (Continued)

(51) Int. Cl.
*G07F 11/00* (2006.01)
*B65H 1/00* (2006.01)
*G07F 9/02* (2006.01)

(Continued)

(52) U.S. Cl.
CPC ............ *G07F 9/026* (2013.01); *G06F 19/3462* (2013.01); *G07F 11/002* (2013.01); *G07F 11/165* (2013.01); *G07F 11/60* (2013.01); *G07F 11/62* (2013.01); *G07F 17/0092* (2013.01)

(58) Field of Classification Search
CPC ................................. G07F 11/00; B65H 1/00
USPC ............ 221/97, 120, 10, 13, 2; 235/381, 382, 235/385; 700/237, 233; 206/466
See application file for complete search history.

(56) References Cited

U.S. PATENT DOCUMENTS

| 1,968,226 A | 7/1934 | Simpkins |
| 3,786,421 A | 1/1974 | Wostl et al. |

(Continued)

FOREIGN PATENT DOCUMENTS

| EP | 2397999 | 12/2011 |
| EP | 2398000 | 12/2011 |

(Continued)

OTHER PUBLICATIONS

Response as filed with the USPTO on Jan. 18, 2012 for U.S. Appl. No. 12/861,767.

(Continued)

*Primary Examiner* — Rakesh Kumar
(74) *Attorney, Agent, or Firm* — Cooley LLP

(57) ABSTRACT

The present invention provides a random access and random load dispensing unit including a housing, at least one support located in the housing and defining a first axis, a plurality of platforms movable along the support along the first axis, a plurality of bins supported on the platforms, the bins being movable with the platforms, and a shuttle assembly movable along the first axis and further movable along a second axis substantially perpendicular to the first axis between the plurality of platforms to access and retrieve products stored in the bins.

31 Claims, 24 Drawing Sheets

Related U.S. Application Data continuation-in-part of application No. 10/801,321, filed on Mar. 16, 2004, now Pat. No. 7,123,989.

(60) Provisional application No. 60/484,544, filed on Jul. 1, 2003, provisional application No. 60/576,005, filed on Jun. 1, 2004, provisional application No. 60/484,544, filed on Jul. 1, 2003.

(51) Int. Cl.
| | | |
|---|---|---|
| G06F 19/00 | (2011.01) | |
| G07F 11/16 | (2006.01) | |
| G07F 11/60 | (2006.01) | |
| G07F 11/62 | (2006.01) | |
| G07F 17/00 | (2006.01) | |

(56) References Cited

U.S. PATENT DOCUMENTS

| | | | |
|---|---|---|---|
| 3,941,977 | A | 3/1976 | Voss et al. |
| 3,943,335 | A | 3/1976 | Kinker et al. |
| 4,359,631 | A | 11/1982 | Lockwood et al. |
| 4,456,122 | A | 6/1984 | Kalal |
| 4,519,522 | A * | 5/1985 | McElwee ............... 221/13 |
| 4,546,901 | A * | 10/1985 | Buttarazzi ............... 221/10 |
| 4,812,629 | A * | 3/1989 | O'Neil et al. ............... 235/383 |
| 4,814,592 | A | 3/1989 | Bradt et al. |
| 4,839,505 | A | 6/1989 | Bradt et al. |
| 4,858,743 | A | 8/1989 | Paraskevakos et al. |
| 4,866,255 | A | 9/1989 | Sing |
| 4,896,024 | A | 1/1990 | Morello et al. |
| 4,951,308 | A | 8/1990 | Bishop et al. |
| 4,995,498 | A | 2/1991 | Menke |
| 5,013,897 | A | 5/1991 | Harman et al. |
| 5,020,958 | A | 6/1991 | Tuttobene |
| 5,036,472 | A * | 7/1991 | Buckley et al. ............... 700/233 |
| 5,042,686 | A | 8/1991 | Stucki |
| 5,059,772 | A | 10/1991 | Younglove |
| 5,088,586 | A * | 2/1992 | Isobe et al. ............... 194/205 |
| 5,095,195 | A | 3/1992 | Harman et al. |
| 5,105,978 | A | 4/1992 | Trouteaud et al. |
| 5,113,351 | A | 5/1992 | Bostic |
| 5,139,384 | A | 8/1992 | Tuttobene |
| 5,143,193 | A | 9/1992 | Geraci |
| 5,159,560 | A | 10/1992 | Newell et al. |
| 5,172,829 | A | 12/1992 | Dellicker, Jr. |
| 5,205,436 | A | 4/1993 | Savage |
| 5,212,649 | A | 5/1993 | Pelletier et al. |
| 5,217,082 | A | 6/1993 | Serra-Tosio et al. |
| 5,283,322 | A | 2/1994 | Martin et al. |
| 5,292,029 | A * | 3/1994 | Pearson ............... 221/2 |
| 5,303,844 | A | 4/1994 | Muehlberger |
| 5,313,393 | A * | 5/1994 | Varley et al. ............... 705/28 |
| 5,337,920 | A | 8/1994 | Clausen |
| 5,385,265 | A * | 1/1995 | Schlamp ............... 221/7 |
| 5,404,384 | A | 4/1995 | Colburn et al. |
| 5,408,443 | A | 4/1995 | Weinberger |
| 5,445,294 | A | 8/1995 | Gardner et al. |
| 5,445,295 | A | 8/1995 | Brown |
| 5,468,110 | A | 11/1995 | McDonald et al. |
| 5,482,139 | A | 1/1996 | Rivalto |
| 5,499,707 | A | 3/1996 | Steury |
| 5,502,944 | A | 4/1996 | Kraft et al. |
| 5,593,267 | A | 1/1997 | McDonald et al. |
| 5,597,995 | A | 1/1997 | Williams et al. |
| 5,713,485 | A | 2/1998 | Liff et al. |
| 5,713,487 | A | 2/1998 | Coughlin |
| 5,713,648 | A | 2/1998 | Geib et al. |
| 5,713,847 | A | 2/1998 | Howard, III et al. |
| 5,720,154 | A | 2/1998 | Lasher et al. |
| 5,748,485 | A | 5/1998 | Christiansen et al. |
| 5,790,409 | A | 8/1998 | Fedor et al. |
| 5,797,515 | A | 8/1998 | Liff et al. |
| 5,812,410 | A | 9/1998 | Lion et al. |
| 5,838,575 | A | 11/1998 | Lion |
| 5,839,257 | A | 11/1998 | Soderstrom et al. |
| 5,880,443 | A | 3/1999 | McDonald et al. |
| 5,893,459 | A | 4/1999 | Croft |
| 5,893,697 | A | 4/1999 | Zini et al. |
| 5,907,493 | A | 5/1999 | Boyer et al. |
| 5,930,145 | A | 7/1999 | Yuyama et al. |
| 5,945,651 | A | 8/1999 | Chorosinski et al. |
| 5,963,453 | A | 10/1999 | East |
| 5,971,593 | A | 10/1999 | McGrady |
| 6,003,006 | A | 12/1999 | Colella et al. |
| 6,021,392 | A | 2/2000 | Lester et al. |
| 6,039,251 | A | 3/2000 | Holowko et al. |
| 6,068,156 | A | 5/2000 | Liff et al. |
| 6,131,399 | A | 10/2000 | Hall |
| 6,152,364 | A | 11/2000 | Schoonen et al. |
| 6,170,230 | B1 | 1/2001 | Chudy et al. |
| 6,199,720 | B1 | 3/2001 | Rudick et al. |
| 6,202,923 | B1 | 3/2001 | Boyer et al. |
| 6,219,587 | B1 * | 4/2001 | Ahlin et al. ............... 700/233 |
| 6,230,927 | B1 * | 5/2001 | Schoonen et al. ............... 221/10 |
| 6,230,930 | B1 | 5/2001 | Sorensen et al. |
| 6,256,967 | B1 | 7/2001 | Hebron et al. |
| 6,263,259 | B1 | 7/2001 | Bartur |
| 6,283,322 | B1 | 9/2001 | Liff et al. |
| 6,305,377 | B1 | 10/2001 | Portwood et al. |
| 6,324,520 | B1 | 11/2001 | Walker et al. |
| 6,330,491 | B1 | 12/2001 | Lion |
| 6,352,200 | B1 | 3/2002 | Schoonen et al. |
| 6,354,498 | B1 | 3/2002 | Lutz |
| 6,370,841 | B1 | 4/2002 | Chudy et al. |
| 6,393,339 | B1 | 5/2002 | Yeadon |
| 6,397,126 | B1 | 5/2002 | Nelson |
| 6,397,193 | B1 | 5/2002 | Walker et al. |
| 6,416,270 | B1 | 7/2002 | Steury et al. |
| 6,421,579 | B1 | 7/2002 | Dimitri et al. |
| 6,438,451 | B1 | 8/2002 | Lion |
| 6,443,359 | B1 | 9/2002 | Green et al. |
| 6,449,627 | B1 | 9/2002 | Baer et al. |
| 6,449,927 | B2 | 9/2002 | Hebron et al. |
| 6,464,142 | B1 | 10/2002 | Denenberg et al. |
| 6,471,089 | B2 | 10/2002 | Liff et al. |
| 6,499,627 | B2 | 12/2002 | Arai |
| 6,505,754 | B1 | 1/2003 | Kenny et al. |
| 6,522,772 | B1 | 2/2003 | Morrison et al. |
| 6,529,801 | B1 * | 3/2003 | Rosenblum ............... 700/237 |
| 6,530,282 | B1 | 3/2003 | Kurtz et al. |
| 6,533,170 | B1 | 3/2003 | Kit |
| 6,539,282 | B2 | 3/2003 | Metcalf et al. |
| 6,556,889 | B2 | 4/2003 | Rudick et al. |
| 6,564,121 | B1 | 5/2003 | Wallace et al. |
| 6,581,798 | B2 | 6/2003 | Liff et al. |
| 6,584,309 | B1 | 6/2003 | Whigham |
| 6,588,548 | B1 * | 7/2003 | Dewitt ............... 186/2 |
| 6,594,549 | B2 | 7/2003 | Siegel |
| 6,597,970 | B1 | 7/2003 | Steury et al. |
| 6,611,810 | B1 | 8/2003 | Kolls |
| 6,644,455 | B2 | 11/2003 | Ichikawa |
| 6,648,153 | B2 | 11/2003 | Holmes |
| 6,697,704 | B2 | 2/2004 | Rosenblum |
| 6,711,460 | B1 | 3/2004 | Reese |
| 6,711,465 | B2 | 3/2004 | Tomassi |
| 6,766,218 | B2 | 7/2004 | Rosenblum |
| 6,814,255 | B2 | 11/2004 | Liff et al. |
| 6,847,861 | B2 * | 1/2005 | Lunak et al. ............... 700/242 |
| 6,874,664 | B1 | 4/2005 | Montgomery |
| 6,874,684 | B1 * | 4/2005 | Denenberg et al. ............... 235/381 |
| 6,877,655 | B1 | 4/2005 | Robertson et al. |
| 6,892,041 | B1 | 5/2005 | Shehata et al. |
| 6,892,941 | B2 | 5/2005 | Rosenblum |
| 6,973,369 | B2 | 12/2005 | Trimmer et al. |
| 7,010,387 | B2 | 3/2006 | Lantry et al. |
| 7,086,558 | B1 | 8/2006 | Pixley et al. |
| 7,093,755 | B2 | 8/2006 | Jordan et al. |
| 7,123,989 | B2 | 10/2006 | Pinney et al. |
| 7,194,333 | B2 | 3/2007 | Shoenfeld |
| 7,228,200 | B2 | 6/2007 | Baker et al. |
| 7,264,136 | B2 | 9/2007 | Willoughby et al. |
| 7,410,098 | B2 | 8/2008 | Denenberg et al. |
| 7,444,203 | B2 | 10/2008 | Rosenblum |

(56) References Cited

U.S. PATENT DOCUMENTS

| | | | |
|---|---|---|---|
| 7,451,015 B2 | 11/2008 | Mazur et al. |
| 7,469,820 B2 | 12/2008 | Rosenblum |
| 7,471,993 B2 | 12/2008 | Rosenblum |
| 7,490,054 B2 | 2/2009 | Reade et al. |
| 7,537,155 B2 | 5/2009 | Denenberg et al. |
| 7,596,427 B1 | 9/2009 | Frederick et al. |
| 7,689,318 B2 | 3/2010 | Draper |
| 7,774,097 B2 | 8/2010 | Rosenblum |
| 7,783,378 B2 | 8/2010 | Pinney et al. |
| 7,787,986 B2 | 8/2010 | Pinney et al. |
| 7,857,161 B2 | 12/2010 | Pinney et al. |
| 8,000,836 B2 | 8/2011 | Pinney et al. |
| 2002/0139810 A1 | 10/2002 | Yuyama et al. |
| 2002/0166787 A1 | 11/2002 | Linton |
| 2002/0173875 A1 | 11/2002 | Wallace et al. |
| 2003/0029882 A1 | 2/2003 | Yuyama et al. |
| 2004/0113786 A1* | 6/2004 | Maloney .................... 340/568.1 |
| 2004/0164146 A1 | 8/2004 | Rosenblum |
| 2004/0215369 A1 | 10/2004 | Rosenblum |
| 2005/0023286 A1 | 2/2005 | Pinney et al. |
| 2005/0049746 A1 | 3/2005 | Rosenblum |
| 2005/0192705 A1 | 9/2005 | Pinney et al. |
| 2006/0265102 A1* | 11/2006 | Bain ............................ 700/237 |
| 2006/0272976 A1 | 12/2006 | Pinney et al. |
| 2007/0010910 A1 | 1/2007 | Pinney et al. |
| 2007/0162183 A1 | 7/2007 | Pinney et al. |
| 2007/0162184 A1 | 7/2007 | Pinney et al. |
| 2010/0268377 A1 | 10/2010 | Pinney et al. |
| 2011/0046778 A1 | 2/2011 | Pinney et al. |
| 2011/0047043 A1* | 2/2011 | Beane et al. ............... 705/26.25 |

FOREIGN PATENT DOCUMENTS

| | | |
|---|---|---|
| WO | WO 00/34925 | 6/2000 |
| WO | WO-01/31593 | 5/2001 |
| WO | WO-02/21402 | 3/2002 |
| WO | WO-2004/021289 | 3/2004 |
| WO | WO-2005/005266 | 1/2005 |

OTHER PUBLICATIONS

US Notice of Allowance dated Jan. 26, 2012 for U.S. Appl. No. 12/861,634.
Automed Efficiency Pharmacy™ R1000 product literature; published or in public use at least as early as Jun. 30, 2002; 2 pages.
Automed Efficiency Pharmacy™ R400 product literature; published or in public use at least as early as Jun. 30, 2002; 2 pages.
Automed Efficiency Pharmacy™ R600 product literature; published or in public use at least as early as Jun. 30, 2002; 2 pages.
Automed Efficiency Pharmacy™ R800 product literature; published or in public use at least as early as Jun. 30, 2002; 2 pages.
Automed™ Technologies ADDS (Automatic Drug Dispensing System) product literature; published or in public use at least as early as Jun. 30, 2002; 1 page.
Automed™ Technologies ATC™ Profile System product literature; published or in public use at least as early as Jun. 30, 2002; 2 pages.
Automed™ Technologies Automed Efficiency Pharmacy™ product literature; published or in public use at least as early as Jun. 30, 2002; 6 pages.
Automed™ Technologies Fastfill™ System product literature; published or in public use at least as early as Jun. 30, 2002; 2 pages.
Automed™ Technologies Optilfill-II System product literature; published or in public use at least as early as Jun. 30, 2002; 4 pages.
Automed™ Technologies Quickfill Plus product literature; published or in public use at least as early as Jun. 30, 2002; 1 page.
Automed® Fastpak™ Tabletop System product literature; published or in public use at least as early as Jun. 30, 2002; 2 pages.
Automed® Fastpak™ 330 and 520 product literature; published or in public use at least as early as Jun. 30, 2002; 4 pages.
Automed® Fastpak™ 71 System product literature; published or in public use at least as early as Jun. 30, 2002; 2 pages.
Automed® Technologies Quickfill product literature; published or in public use at least as early as Jun. 30, 2002; 1 page.
Barker et al, White Paper on Automation in Pharmacy, The Consultant Pharmacists, 13(13):21-37, Mar. 1996.
CBS News, Automated Medicine, Nov. 13, 2001, available at http://www.cbsnews.com/stories/2001/11/13/health/printable317894.shtml
Chains, Independents make some gains in technology, Drugtopics.com, Dec. 10, 2001, 3 pgs.
Declaration of Daniel Bain: executed Sep. 2004; 2 pages.
Declaration of Walter Bain including Exhibit A; executed Sep. 2004; 6 pages.
Docs try ATM-style prescription machines, CNN.com. Nov. 17, 2001, 2 pgs.
EP Office Action dated Sep. 24, 2009 for EP Application No. 05825427.7.
EP Office Action dated Oct. 13, 2009 for EP Application No. 04756405.9.
EP Search Report dated Jun. 22, 2006 for EP Application No. 04756405.9.
Express Scripts company literature; published or in public use at least as early as Jun. 30, 2002; 2 pages.
Extended European Search Report dated Jun. 29, 2009 for EP Application No. 05825427.7.
Fleming, Harris, Jr., Orderly Process—Can central prescription filling help solve pharmacy's time crunch? McKesson thinks it can, DrugTopics.com, Mar. 1, 1999, 3 pgs.
Foundation Systems Automated Prescription Point-of-Delivery Kiosk System product literature; published or in public use at least as early as Jun. 30, 2002; 1 page.
GSL Solutions Will-Call Storage Systems product literature; published or in public use at least as early as Jun. 30, 2002; 4 pages.
Innovation Associates PharmASSIST Robotic Dispensing Systems (RDS-I and RDS-II) product literature; published or in public use at least as early as Jun. 30, 2002; 2 pages.
Innovation Associates SmartCabinet System product literature; published or in public use at least as early as Jun. 30, 2002; 2 pages.
International Search Report and Written Opinion of the International Searching Authority dated Feb. 23, 2007 for PCT/US05/43243.
International Search Report dated Mar. 10, 2005 for PCT Application No. PCT/US2004/020978.
Jackman, Michael, Study says chain drug stores ripe for kiosks, KioskMarketPlace.com, Aug. 1, 2001, 2 pgs.
Kieser, Joe, Medication available at punch of a button, Sun Newspapers, Oct. 31, 2001, 2 pgs.
Letter from Daniel T. Jones; dated May 15, 2001; 1 page.
Lewis et al, Developing the Infrastructure for Patient Care, The Patient-Centered Pharmacy, APhA, 2002, pp. 66-94.
McKesson Accu Script™ Pharmacy Robot product literature; published or in public use at least as early as Jun. 30, 2002; 2 pages.
McKesson Accumed™ powered by Auto Link™ product literature; published or in public use at least as early as Jun. 30, 2002; 2 pages.
McKesson APS: Automated Will Call Rotary Cabinet, available at http://www.mckessonaps.com/wt/aps/prodserv_profiles_willcall.
McKesson Automated Will Call™ product literature; published or in public use at least as early as Jun. 30, 2002; 1 page.
McKesson Baker Cassettes™ product literature; published or in public use at least as early as Jun. 30, 2002; 1 page.
McKesson Baker Cells™ product literature; published or in public use at least as early as Jun. 30, 2002; 1 page.
McKesson MedCarousel™ product literature; published or in public use at least as early as Jun. 30, 2002; 2 pages.
MedVantx Point-of-Care Automated Sample System product literature; published or in public use at least as early as Jun. 30, 2002; 1 page.
Mendota Healthcare, Inc. Business Plan: Dec. 1, 2001; 36 pages.
Mendota Healthcare, Inc. Executive Summary; copyright 2001; 7 pages.
Mendota Healthcare, Inc.'s profile of "InstyMeds" available at www.instymed.com.video.html, 12 pgs.
Mentroy, Jill S., MD, FACS, Telepharmacy: VA Pharmacy finds Convenience in Vending Machines, Veterans Health System Journal (VHSJ), Oct. 6, 1998, 2 pgs.

(56) References Cited

OTHER PUBLICATIONS

NCR Fastlane™—The Self-Checkout Solution product literature; published or in public use at least as early as Jun. 30, 2002; 8 pages.
NCR Instymeds Prescription Medication Dispenser product literature; published or in public use at least as early as Jun. 30, 2002; 8 pages.
Parata Systems Parata RDS product literature; published or in public use at least as early as Jun. 30, 2002; 3 pages.
Pending claims for U.S. Appl. No. 11/688,183.
Pickpoint Corporation's profile of FlexCall product available at http://www.pickpoint.com/products~flexcall.html, 23 pgs.
Pickpoint™ FlexRx™ Pharmacy Dispensing product literature; published or in public use at least as early as Jun. 30, 2002; 6 pages.
Pyxis Helpmate® SP product literature; published or in public use at least as early as Jun. 30, 2002; 2 pages.
Pyxis Medstation® 2000 product literature; published or in public use at least as early as Jun. 30, 2002: 1 page.
Pyxis Medstation® 3000 product literature; published or in public use at least as early as Jun. 30, 2002, 1 page.
Pyxis Supplystation® product literature; published or in public use at least as early as Jun. 30, 2002, 4 page.
Request for Continued Examination (RCE) and Amendment as filed with the USPTO on Sep. 8, 2010 for U.S. Appl. No. 11/484, 409.
Request for Continued Examination (RCE) and Amendment as filed with the USPTO on Sep. 18, 2008 for U.S. Appl. No. 11/688,183.
Response as filed with the USPTO on Jan. 8, 2009 for U.S. Appl. No. 11/520/928.
Response as filed with the USPTO on Jan. 11, 2010 for U.S. Appl. No. 11/740,253.
Response as filed with the USPTO on Jan. 25, 2010 for U.S. Appl. No. 11/520,928.
Response as filed with the USPTO on Jan. 29, 2009 for U.S. Appl. No. 11/484,409.
Response as filed with the USPTO on Mar. 1, 2010 for U.S. Appl. No. 11/484,409.
Response as filed with the USPTO on Mar. 8, 2009 for U.S. Appl. No. 11/688,183.
Response as filed with the USPTO on Apr. 14, 2009 for U.S. Appl. No. 10/880,269.
Response as filed with the USPTO on Apr. 22, 2009 for U.S. Appl. No. 11/688,183.
Response as filed with the USPTO on Apr 22, 2009 for U.S. Appl. No. 11/688,189.
Response as filed with the USPTO on Apr. 22, 2009 for U.S. Appl. No. 11/520,928.
Response as filed with the USPTO on May 22, 2006 for U.S. Appl. No. 10/801,321.
Response as filed with the USPTO on May 22, 2008 for U.S. Appl. No. 11/688,183.
Response as filed with the USPTO on May 27, 2009 for U.S. Appl. No. 11/484,409.
Response as filed with the USPTO on Jul. 9, 2010 for U.S. Appl. No. 11/520,928.
Response as filed with the USPTO on Aug. 9, 2010 for U.S. Appl. No. 11/484,409.
Response as filed with the USPTO on Aug. 23, 2007 for U.S. Appl. No. 11/688,189.
Response as filed with the USPTO on Sep. 12, 2008 for U.S. Appl. No. 11/688,189.
Response as filed with the USPTO on Sep. 15, 2009 for U.S. Appl. No. 11/484,409.
Response as filed with the USPTO on Sep. 15, 2009 for U.S. Appl. No. 11/520,928.
Response as filed with the USPTO on Sep 15, 2009 for U.S. Appl. No. 11/688,183.
Response as filed with the USPTO on Oct. 19, 2007 for U.S. Appl. No. 11/688,183.
Response as filed with the USPTO on Nov. 29, 2007 for U.S. Appl. No. 11/688,189.
Response as filed with the USPTO on Dec. 29, 2009 for U.S. Appl. No. 11/688,189.
Rowland, Christopher, Drug Vending Units Worry Pharmacists, Jul. 3, 2004, 3 pages.
Scriptpro® Pharmacy Automation SP 100™ Robotic Prescription Dispensing System product literature; published or in public use at least as early as Jun. 30, 2002, 2 pages.
Scriptpro® Pharmacy Automation SP 200® Robotic Prescription Dispensing System product literature; published or in public use at least as early as Jun. 30, 2002, 2 pages.
Scriptpro® Pharmacy Automation SP Automation Center™ (SPace™) product literature; published or in public use at least as early as Jun. 30, 2002; 2 pages.
Scriptpro® Pharmacy Automation SP Central® Pharmacy Dispensing Management System product literature; published or in public use at least as early as Jun. 30, 2002; 1 page.
Scriptpro® Pharmacy Automation SP Station® product literature: published or in public use at least as early as Jun. 30, 2002; 2 pages.
Scriptpro® Pharmacy Automation SP Unit Dispenser™ (SPUD®) Robotic Pharmaceutical Dispensing System product literature; published or in public use at least as early as Jun. 30, 2002; 2 pages.
Telepharmacy Solutions, Inc. profile TSI's ADDS (Automated Drug Distribution System) product available at http://www.telepharmaysolutions.com, 44 pgs.
Time to switch drugstores?, Consumer Reports, Oct. 2003, 5 pgs.
Ukens, Carol, "Pharmacist Shortage Boosts Telepharmacy", Telepharmacy Solutions Media Coverage. Jun. 3, 2002. 2 pgs.
Ukens, Carol, Another automated dispenser hits community pharmacy, Drugtopics.com, Sep. 15, 1997, 3 pgs.
Ukens, Carol, Remote Control—Automation puts retail R.Ph.'s foot in doctor's door. Drugtopics.com, Jan. 20, 1997, 3 pgs.
Ukens, Carol, Technology—Rx vending machine targets pharmacy, Drugtopics.com, Dec. 10, 2001, 3 pgs.
US Advisory Action dated Mar. 18, 2008 for U.S. Appl. No. 11/686,183.
US Advisory Action dated Aug. 25, 2010 for U.S. Appl. No. 11/484,409.
US Notice of Allowability dated Feb. 18, 2010 for U.S. Appl. No. 11/688,189.
US Notice of Allowance dated Jan. 27, 2010 for U.S. Appl. No. 11/688,189.
US Notice of Allowance dated Apr. 19, 2010 for U.S. Appl. No. 11/688,183.
US Notice of Allowance dated Apr. 19, 2010 for U.S. Appl. No. 11/740,253.
US Notice of Allowance dated Jun. 14, 2006 for U.S. Appl. No. 10/880,269.
US Notice of Allowance dated Jul. 19, 2006 for U.S. Appl. No. 10/801,321.
US Notice of Allowance dated Aug. 19, 2010 for U.S. Appl. No. 11/520,928.
US Office Action dated Jan. 9, 2007 for U.S. Appl. No. 11/001,110.
US Office Action dated Feb. 22, 2006 for U.S. Appl. No. 10/801,321.
US Office Action dated Mar. 15, 2006 for U.S. Appl. No. 10/880,269.
US Office Action dated Mar. 28, 2008 for U.S. Appl. No. 11/688,183.
US Office Action dated Apr. 2, 2009 for U.S. Appl. No. 11/520,928.
US Office Action dated Apr. 28, 2009 for U.S. Appl. No. 11/484,409.
US Office Action dated May 23, 2007 for U.S. Appl. No. 11/688,189.
US Office Action dated May 26, 2010 for U.S. Appl. No. 11/520,928.
US Office Action dated Jun. 8, 2010 for U.S. Appl. No. 11/484,409.
US Office Action dated Jun. 13, 2003 for U.S. Appl. No. 11/688,189.
US Office Action dated Jun. 18, 2008 for U.S. Appl. No. 11/688,183.
US Office Action dated Jul. 19, 2007 for U.S. Appl. No. 11/688,183.
US Office Action dated Aug. 18, 2009 for U.S. Appl. No. 11/688,183.
US Office Action dated Aug. 19, 2009 for U.S. Appl. No. 11/484,409.
US Office Action dated Aug. 19, 2009 for U.S. Appl. No. 11/520,928.
US Office Action dated Sep. 12, 2009 for U.S. Appl. No. 11/001,110.
US Office Action dated Oct. 16, 2009 for U.S. Appl. No. 11/740,253.
US Office Action dated Oct. 22, 2008 for U.S. Appl. No. 11/484,409.
US Office Action dated Nov. 2, 2007 for U.S. Appl. No. 11/688,189.
US Office Action dated Nov. 21, 2005 for U.S. Appl. No. 10/801,321.
US Office Action dated Nov. 22, 2010 for U.S. Appl. No. 12/777,181.
US Office Action dated Nov. 25, 2009 for U.S. Appl. No. 11/688,189.

(56) References Cited

OTHER PUBLICATIONS

US Office Action dated Dec. 1, 2009 for U.S. Appl. No. 11/484,409.
US Office Action dated Dec. 4, 2009 for U.S. Appl. No. 11/520,926.
US Office Action dated Dec. 12, 2008 for U.S. Appl. No. 11/520,928.
US Office Action dated Dec. 22, 2008 for U.S. Appl. No. 11/688,183.
US Office Action dated Dec. 22, 2009 for U.S. Appl. No. 11/688,169.
Vending Pharmacy—Is the long-distance dispensing of drugs the remedy for patients in remote areas?, Drugtopics.com, Mar. 6, 2000, 3 pgs.
US Notice of Allowance dated Jan. 31, 2012 for U.S. Appl. No. 12/861,767.
Response as filed with the USPTO on Mar. 18, 2011 for U.S. Appl. No. 12/777,181.
Canadian Office Action dated Mar. 7, 2011 for CA Application No. 2533754.
US Notice of Allowance dated Apr. 6, 2011 for U.S. Appl. No. 12/777,181.
US Office Action dated Apr. 7, 2011 for U.S. Appl. No. 12/861,767.
US Office Action dated Mar. 13, 2013 for U.S. Appl. No. 13/345,070.
US Notice of Allowance dated Apr. 26, 2012 for U.S. Appl. No. 13/345,070.
Examination Report dated Apr. 12, 2011 for EP Application No. 05825427.7.
Summons to Attend Oral Proceedings Pursuant to Rule 115(1) EPC dated Jun. 3, 2013 for EP Application No. 05825427.7.
Canadian Office Action dated Aug. 7, 2013 for CA Application No. 2589530.
European Examination Report dated Oct. 18, 2012 for European Application No. 11181648.4.
European Examination Report dated Oct. 18, 2012 for European Application No. 11181649.2.
European Search Report dated Nov. 7, 2011 for EP Application No. 11181649.2.
European Search Report dated Nov. 7, 2011 for EP Application No. 1181648.4.
Response as filed with the USPTO on Oct. 6, 2011 for U.S. Appl. No. 12/861,767.
Response as filed with the USTPO on Dec. 21, 2011 for U.S. Appl. No. 12/861,634.
Response to CA Office Action filed on Sep. 2, 2011 for CA Application No. 2533754.
Response to EP Examination Report filed on Aug. 9, 2011 for EP Application No. 05825427.7.
US Office Action dated Jan. 9, 2008 for U.S. Appl. No. 11/688,183.
US Office Action dated Jun. 13, 2008 for U.S. Appl. No. 11/688,189.
US Office Action dated Dec. 22, 2008 for U.S. Appl. No. 11/688,189.

\* cited by examiner

RANDOM ACCESS AND RANDOM LOAD DISPENSING UNIT

RELATED APPLICATIONS

This application is a continuation of U.S. patent application Ser. No. 11/520,928, filed Sep. 13, 2006, now U.S. Pat. No. 7,857,161, which is divisional of U.S. patent application Ser. No. 10/880,269, filed Jun. 29, 2004, now abandoned, which is a continuation-in-part of U.S. patent application Ser. No. 10/801,321 filed Mar. 16, 2004, now U.S. Pat. No. 7,123,989. This application also claims priority to U.S. Provisional Patent Application. No. 60/484,544, filed Jun. 30, 2003 and U.S. Provisional Patent Application No. 60/576,005, filed Jun. 1, 2004. All of the above-identified applications are incorporated herein by reference.

FIELD OF THE INVENTION

The present invention relates generally to dispensing units for dispensing items to individuals and, more particularly, to automated or computer-controlled dispensing units.

BACKGROUND OF THE INVENTION

The typical pharmaceutical transaction entails a doctor ordering a prescription for a patient, the prescription being delivered to a pharmacy, and the patient/customer picking up the finished prescription from the pharmacy.

The typical transaction requires face-to-face interaction between the patient/customer and an available pharmacist, technician, or clerk in order to receive or pick up the finished or filled prescription. In conventional settings, a customer may be required to wait in line to drop off and/or pick up a finished prescription. Further, when the customer can pick up the prescription may be constrained by the hours that a particular pharmacy is open for business. This may result in lost potential sales to a retail establishment in which a pharmacy is located because the customer may cancel a trip to the retail establishment that they otherwise might have made had the pharmacy been open. This may also result in a delay for the customer to pick up time-sensitive prescriptions. A device that allows a customer to pick up a finished prescription without face-to-face contact with pharmacy staff would be welcomed by customers in need of finished prescriptions and the pharmacies serving them.

SUMMARY OF THE INVENTION

The present invention provides, in one aspect, a random access and random load dispensing unit including a housing, at least one support located in the housing and defining a first axis, a plurality of platforms movable along the support along the first axis, a plurality of bins supported on the platforms, the bins being movable with the platforms, and a shuttle assembly movable along the first axis and further movable along a second axis substantially perpendicular to the first axis between the plurality of platforms to access and retrieve products stored in the bins.

The present invention provides, in another aspect, a random access and random load dispensing unit including a housing, a shuttle assembly movable in the housing to access and retrieve products stored in random locations in the housing, an access door pivotably coupled to the housing, and a plurality of customer interface components coupled to the access door. At least one of the customer interface components is configured to determine an identity of a customer. The dispensing unit also includes a computer in communication with the customer interface components. The computer is able to match the customer with at least one of the products stored in the random locations in the housing. The dispensing unit further includes a controller in communication with the computer for operating the shuttle assembly. The shuttle assembly is directed to the location in the housing to retrieve the at least one product for the customer.

The present invention provides, in yet another aspect, a random access and random load dispensing unit including a housing, an access door pivotably coupled to the housing, and a plurality of customer interface components coupled to the access door. At least one of the customer interface components is configured to determine an identity of a customer. The dispensing unit also includes at least one substantially vertically-oriented support defining a first axis and located in the housing, a plurality of platforms movable along the first axis and coupled to the support, and a plurality of bins supported on the platforms. The bins are movable with the platforms to selectively allow only the bins on one of the plurality of platforms to be accessed at a given time. The dispensing unit further includes a shuttle assembly movable along the first axis. The shuttle assembly is further movable along a second axis and a third axis coplanar with the second axis. The second and third axes are substantially perpendicular to the first axis and to each other. The shuttle assembly is movable along the second and third axes between the plurality of platforms to access and retrieve products stored in the bins. The dispensing unit also includes a computer in communication with the customer interface components. The computer is able to match a particular product previously specified for the customer with a random location in the housing in which the particular product is stored. The dispensing unit further includes a controller in communication with the computer for operating the shuttle assembly. The shuttle assembly is directed to the random location in the housing to retrieve the specific product for the customer. The dispensing unit, also includes a dispense bin located in the access door. The dispense bin is movable between a first position, in which the dispense bin is deployed into the housing for the shuttle assembly to deposit the product into the dispense bin, and a second position, in which the dispense bin is retracted into the access door and the product is ready to be retrieved by the customer. The dispensing unit further includes a dispense bin lid selectively covering the dispense bin. The dispense bin lid is movable between a first position, in which the product in the dispense bin is inaccessible by the customer, and a second position, in which the product in the dispense bin is accessible by the customer for removal.

The present invention provides, in a further aspect, a container for use with a vending apparatus configured to dispense pharmaceuticals, whereby the vending apparatus utilizes an automated picker assembly to retrieve the container. The container includes a receptacle containing the pharmaceuticals, and a substantially rigid header coupled to the receptacle. The header includes opposite end portions extending beyond an outer periphery of the receptacle, two apertures through the header, and a barcode label coupled to the header.

The present invention provides, in another aspect, a container for use with a vending apparatus configured to dispense pharmaceuticals. The vending apparatus utilizes an automated picker assembly to retrieve the container. The container includes a receptacle having an open end to deposit therein the pharmaceuticals, and two opposing side walls defining in part the open end. The container also includes a header having an insertion portion insertable into the open end of the receptacle between the opposing side walls, opposite end portions extending beyond an outer periphery of the receptacle, and two apertures through the header, the apertures each defining a shape having an apex. The container further includes a label having a barcode printed thereon. A first portion of the label is coupled to one of the side walls of the receptacle and to one side of the header. A second portion of the label extends beyond an outer periphery of the header. The second portion of the label is configured to couple to a second side of the header and the other side wall of the receptacle to at least partially close the open end of the receptacle.

Other features and aspects of the present invention will become apparent to those skilled in the art upon review of the following detailed description, claims and drawings.

BRIEF DESCRIPTION OF THE DRAWINGS

In the drawings, wherein like reference numerals indicate like parts.

Figure 1:
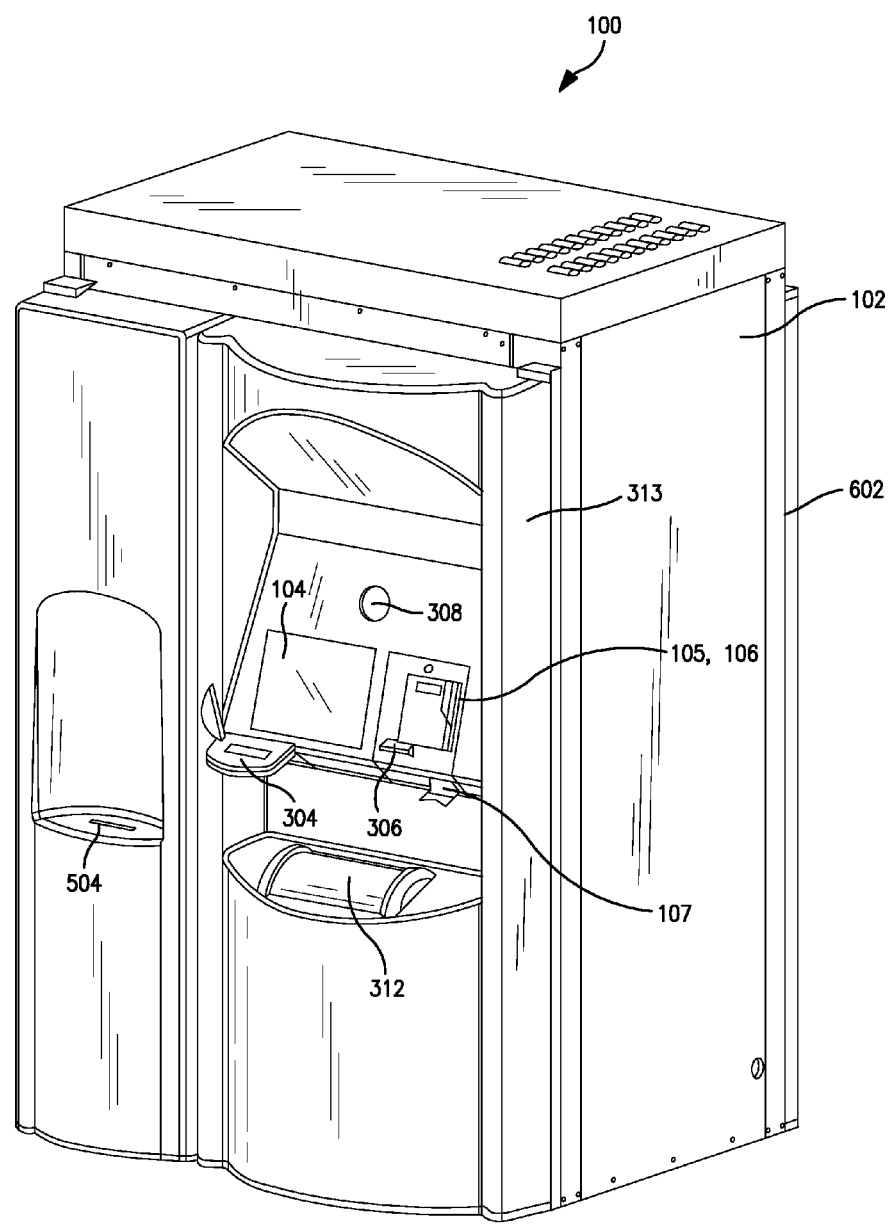
FIG. 1 is a front perspective view of a random access and random load dispensing unit of the present invention.

Before any features of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including", "having", and "comprising" and variations thereof herein is meant to encompass the items listed thereafter and equivalents thereof as well as additional items. The use of letters to identify elements of a method or process is simply for identification and is not meant to indicate that the elements should be performed in a particular order.

DETAILED DESCRIPTION

Figure 2:
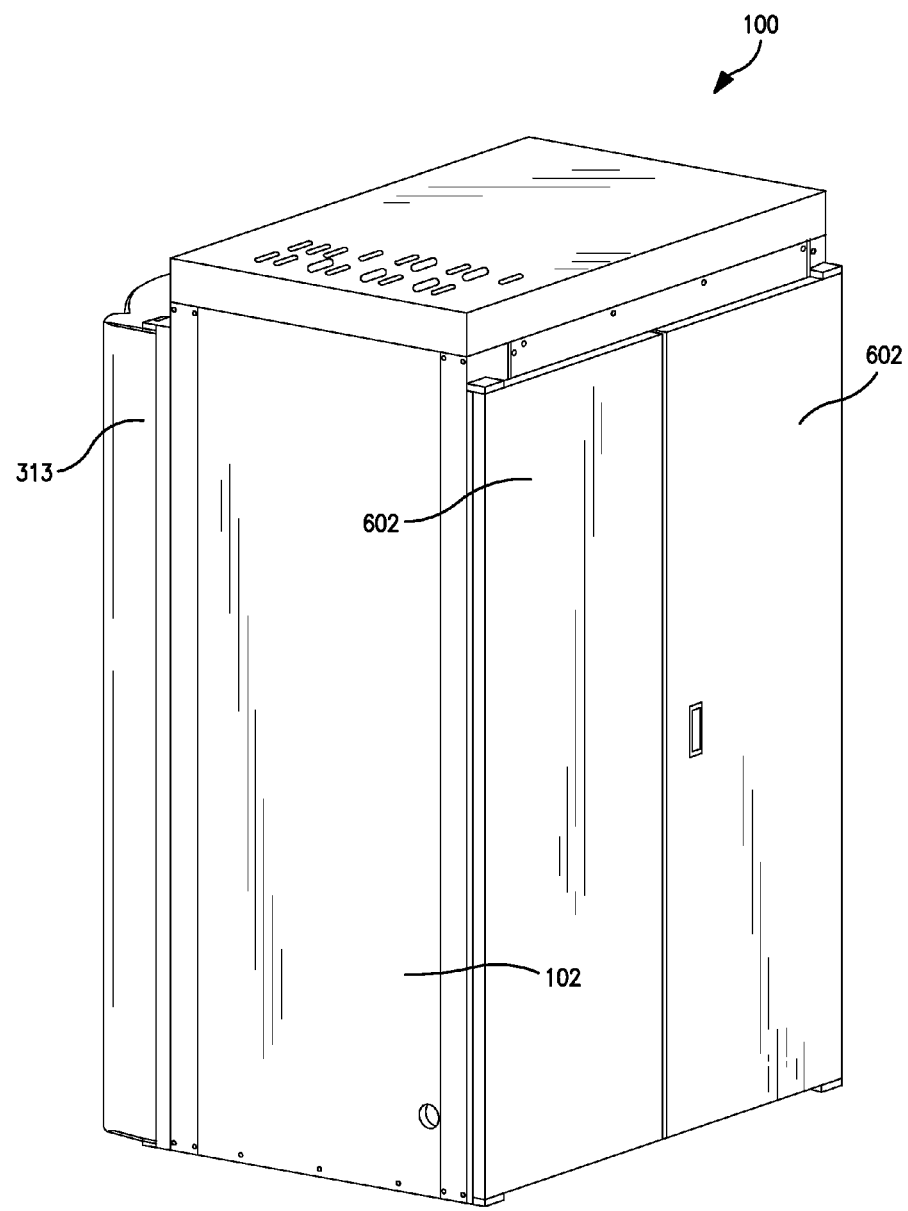
FIG. 2 is a rear perspective view of the dispensing unit of FIG. 1.

FIGS. 1 and 2 illustrate an automated random-access and random-load dispenser or dispensing unit 100 which allows customers to purchase products, particularly prescription medicines. As shown in FIG. 1, the unit 100 includes a housing 102, means to communicate with the customer (e.g., a touch screen 104, or the like), means to identify the customer (e.g., a magnetic stripe card reader 105), and means to accept payment from the customer (e.g., a cash acceptor or a credit card reader 106). The credit card reader 106 can be utilized as the magnetic stripe card reader 105 to identify the customer. The unit 100 may alternatively or additionally include other identification readers, such as a barcode scanner 107 located at the front of the unit 100. The barcode scanner 107 may work in conjunction with customer identification cards (e.g., drivers licenses, etc.) and/or store cards (e.g., prescription drug cards, pharmacy discount cards, customer loyalty cards, etc.), which typically include a barcode to identify the customer. Further, other identification readers may be utilized, such as fingerprint readers and retinal scanners, for example, to identify the customer.

The touch screen 104 can also be utilized by the customer to initiate customer login. For example, the customer can utilize the touch screen 104 to enter a user name or other identifying information, such as a prescription number. The touch screen 104 can further be utilized by the customer to verify their identity by inputting, for example, a password (e.g., a birth date, social security number, etc.) or a personal identification number.

Figure 3:
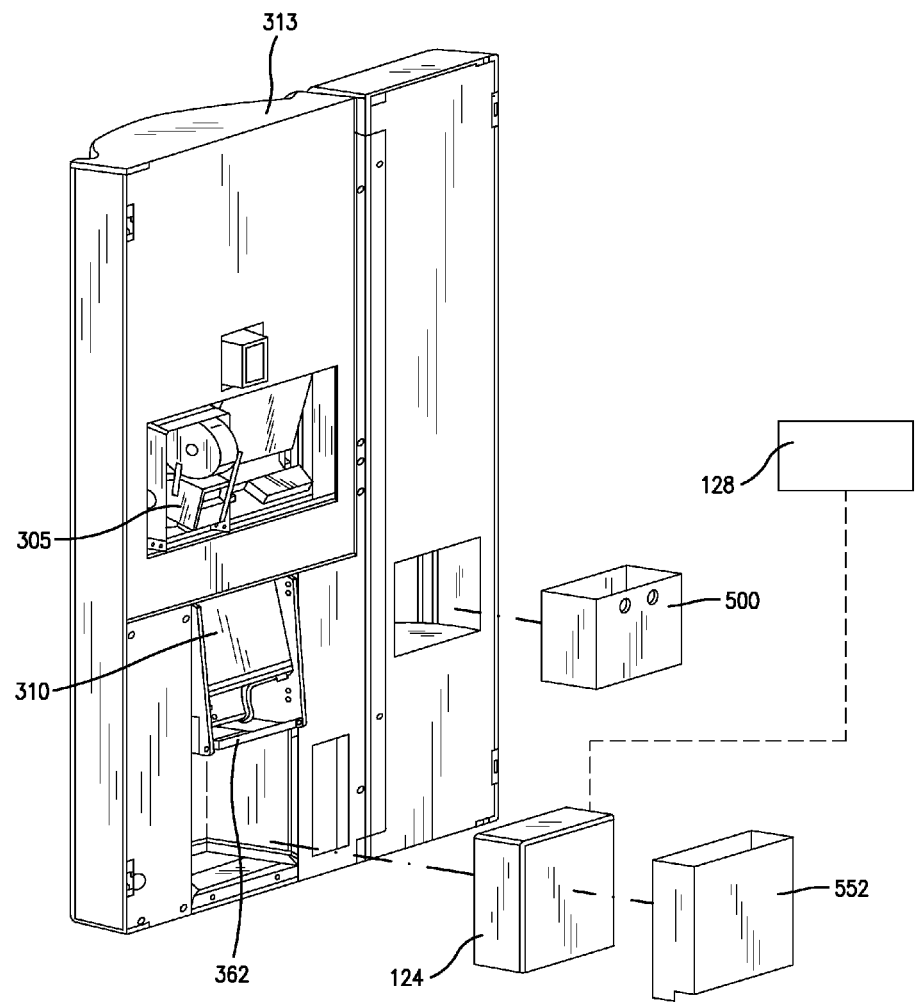
FIG. 3 is a rear perspective view of a portion of the interior of the dispensing unit of FIG. 1, illustrating a portion of the internal components of the dispensing unit.

The unit 100 may also include a signature pad 304 on which the customer may record their signature to complete a purchase. Further, the unit 100 may include a printer 305 (see FIG. 3) to output a receipt (through dispense opening 306) to the customer for a record of the purchase. The unit 100 may also include a camera 308 to monitor and/or record customers' transactions with the unit 100. After a customer completes a transaction with the unit 100, the unit 100 may dispense a finished prescription to a dispense bin 310 (see FIGS. 3-5), which is accessible by the customer through a retractable dispense bin lid 312 (see FIG. 1). The dispense bin 310 and operation thereof will be discussed in greater detail below.

Alternatively, the unit 100 may incorporate more than one touch screen 104, more than one magnetic stripe card reader 105 and/or credit card reader 106, more than one barcode scanner 107, more than one signature pad 304, more than one printer 305, more than one camera 308, and more than one dispense bin 310 to allow more than one customer to utilize the unit 100 at a given time.

The customer interface controls or components, including the touch screen 104, magnetic stripe card reader 105 and/or credit card reader 106, barcode scanner 107, signature pad 304, receipt dispense opening 306, camera 308, and dispense bin 310 are located on an access door 313 coupled to the housing 102. The access door 313 may be pivotably coupled to the housing 102, such that an operator may pivot the access door 313 away from the housing 102 to service the working components of the touch screen 104, magnetic stripe card reader 105 and/or credit card reader 106, barcode scanner 107, signature pad 304, receipt dispense opening 306, camera 308, and dispense bin 310.

The unit 100 may incorporate a prescription drop-off bin 500 (see FIG. 3) to allow a customer to drop off their prescription to be filled. Prescriptions may be inserted through a slot 500 in the access door 313 to be collected by the drop-off bin 500. The prescription drop-off bin 500 may be integrally formed with the access door 313. Alternatively, the prescription drop-off bin 500 may be a separate component from the access door 313 and positioned at a different location on the housing 102. A pharmacist or technician may access the drop-off bin 500 by opening the access door 313 to retrieve the prescriptions deposited in the drop-off bin 500.

The unit 100 also includes a computer 124 that is operable to interface with the touch screen 104, the credit card reader 106, the barcode scanner 107, the signature pad 304, and the receipt printer 305. The computer 124 may be physically located almost anywhere in the unit 100, however, in the illustrated construction, the computer 124 is located in the access door 313 of the unit 100. The computer 124 is shown as a component of the unit 100, but it will be understood by those of ordinary skill in the art that the computer 124 could be remote from the unit 100 and operate the unit 100 through an information connection, such as a network. Further, the computer 124 is shown as dedicated to the unit 100, but multiple units 100 could operate off the same computer 124. The unit 100 would not need its own computer 124, but instead could operate off a computer 124 housed in another unit 100 or not housed within a unit 100 at all. The housing 102 may further include a conveniently located countertop (not shown) to facilitate the customer's interaction with the unit 100.

Figure 4:
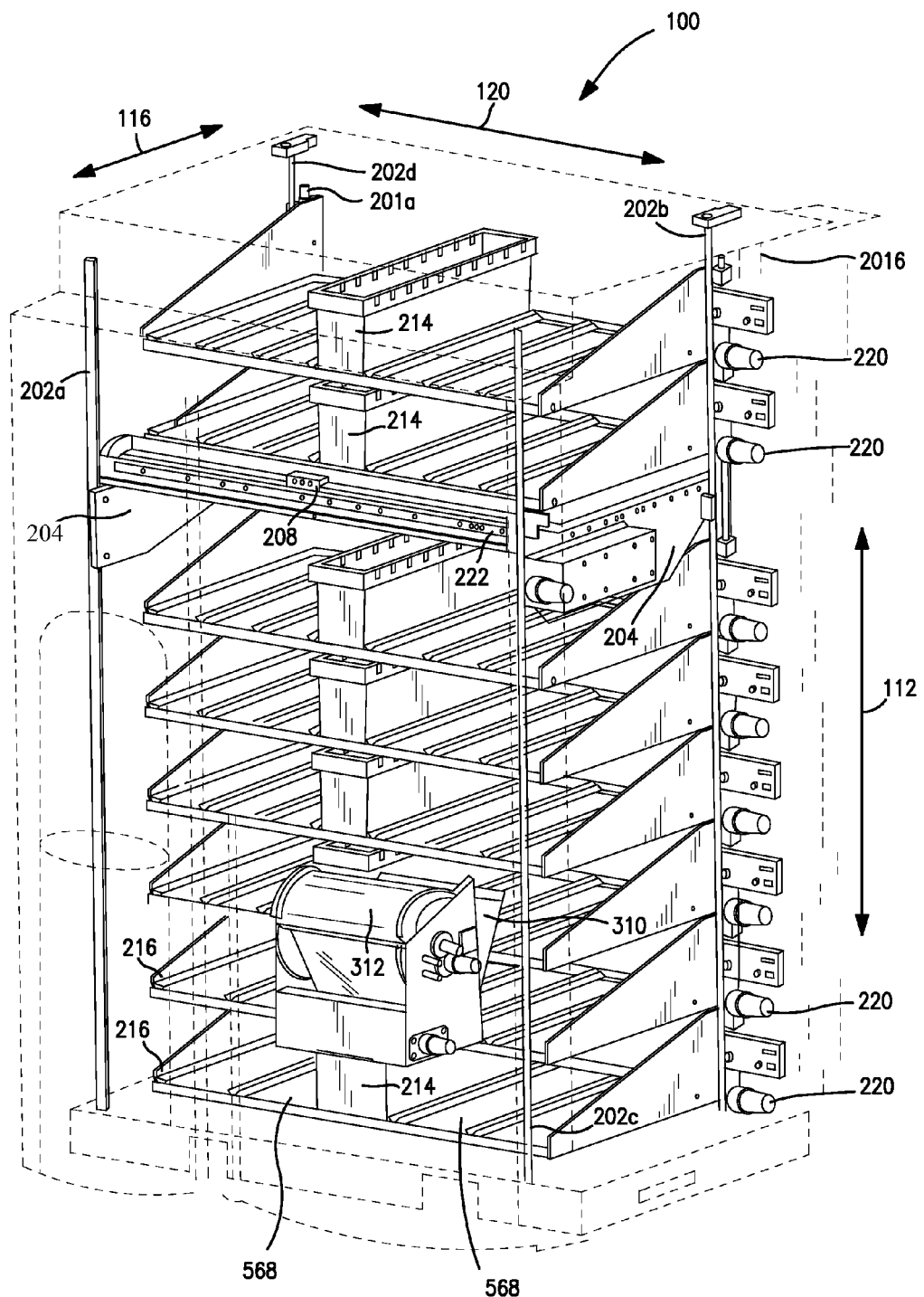
FIG. 4 is a front perspective view of a portion of the internal components of the dispensing unit of FIG. 1.
Figure 5:
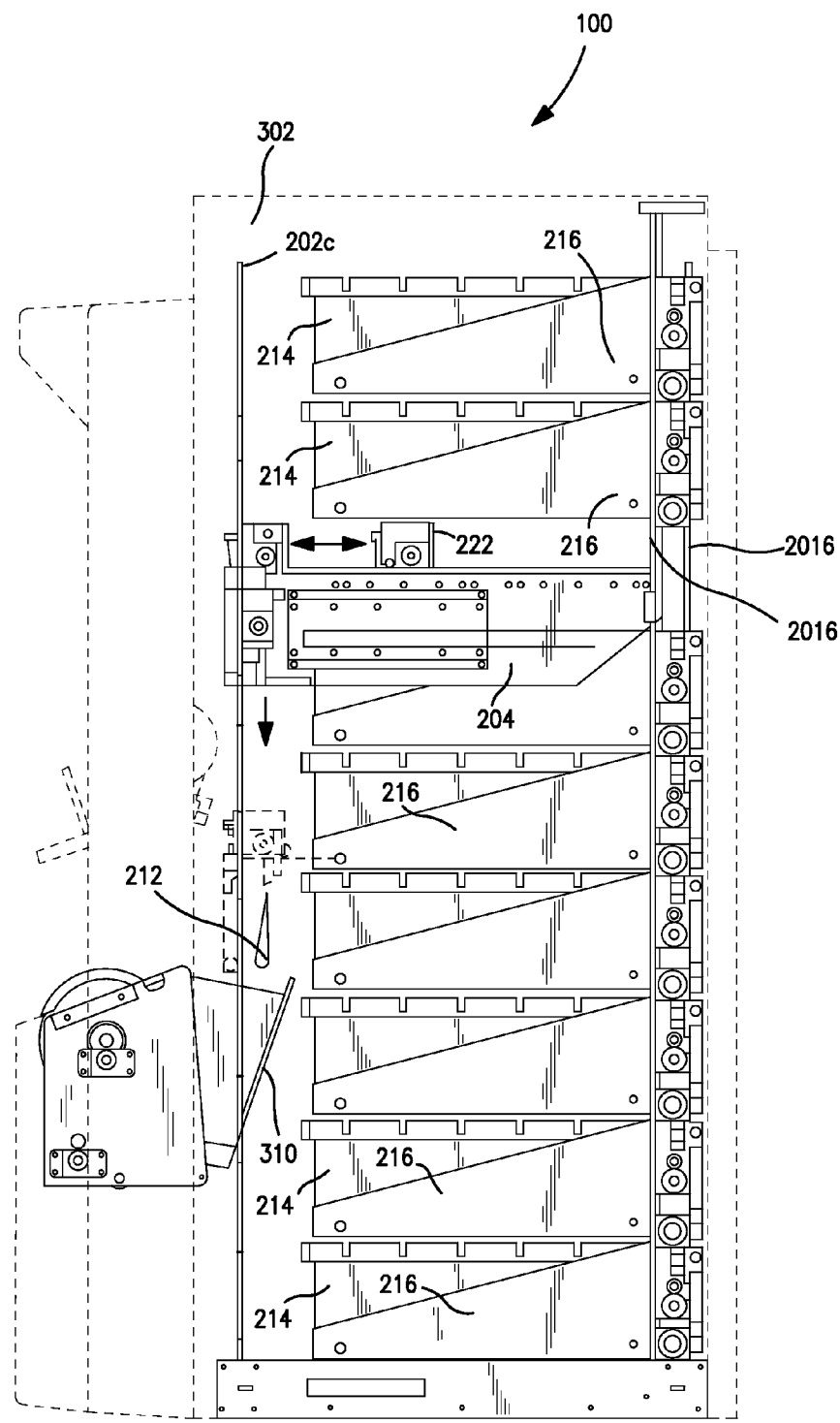
FIG. 5 is a side view of the internal components of the dispensing unit of FIG. 1.

FIGS. 4 and 5 illustrate the internal components of the unit 100. Two vertically-oriented platform support members 201a, 201b support a plurality of platforms 216, such that the platforms 216 are allowed to travel or maneuver along a vertical axis (i.e., Y-axis 112) inside the housing 102. In the illustrated construction of the unit 100, the platforms 216 are cantilevered off of the support members 201a, 201b. However, in alternative constructions of the unit 100, additional support members may be utilized to support the front portions of the platforms 216.

A plurality of vertically-oriented, or "Y-axis" support members 202a-202d support a picker or shuttle assembly 208, such that the shuttle assembly 208 is allowed to travel or maneuver along a vertical axis (i.e., Y-axis 112) inside the housing 102. In addition, an "X-axis" support 222 or a carriage (also see FIGS. 8-10) allows the shuttle assembly 208 to travel or maneuver from side to side in the housing 102 (i.e., along X-axis 120). Further, "Z-axis" supports 204 or carriage supports (see FIGS. 4, 5, and 10) allow the shuttle assembly 208 to travel or maneuver from the front of the housing 102 to the rear of the housing 102 (i.e., along Z-axis 116). The Y-axis supports 202a-202d, the X-axis support 222, and the Z-axis supports 204 combine to provide a support structure allowing the shuttle assembly 208 to travel to any defined location within the housing 102.

Figure 6:
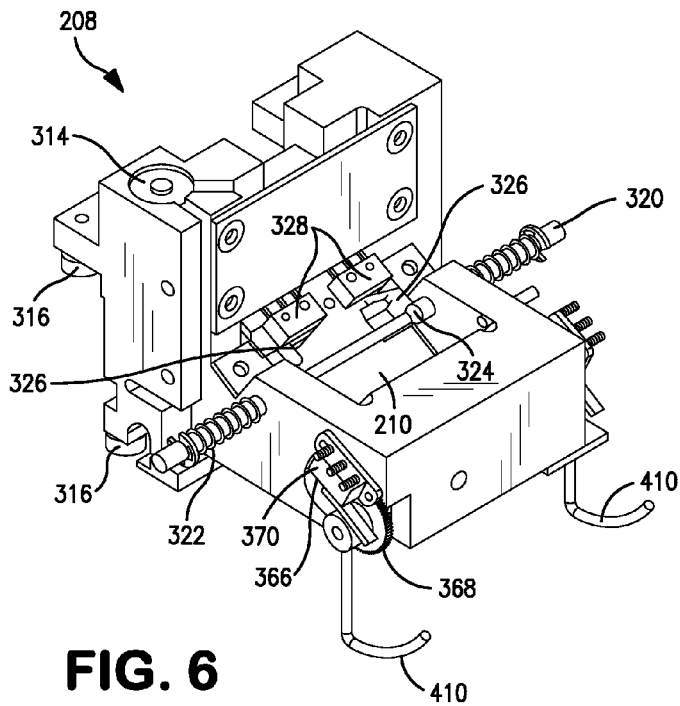
FIG. 6 is a top perspective view of a shuttle assembly of the dispensing unit of FIG. 1.
Figure 7:
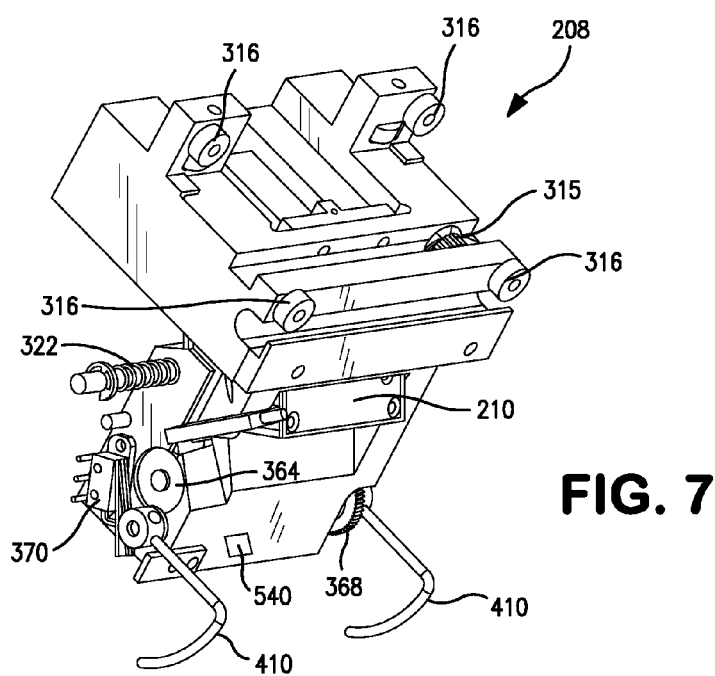
FIG. 7 is a bottom perspective view of the shuttle assembly of FIG. 6.
Figure 8:
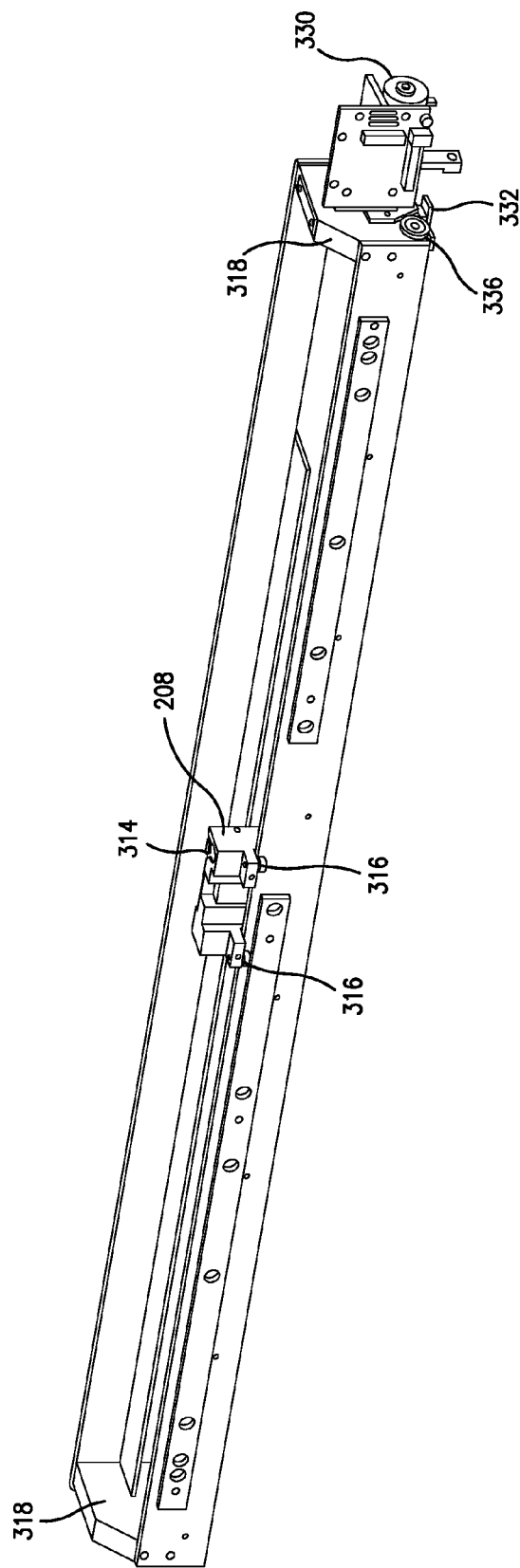
FIG. 8 is a front perspective view of a carriage and the shuttle assembly of the dispensing unit of FIG. 1.
Figure 9:
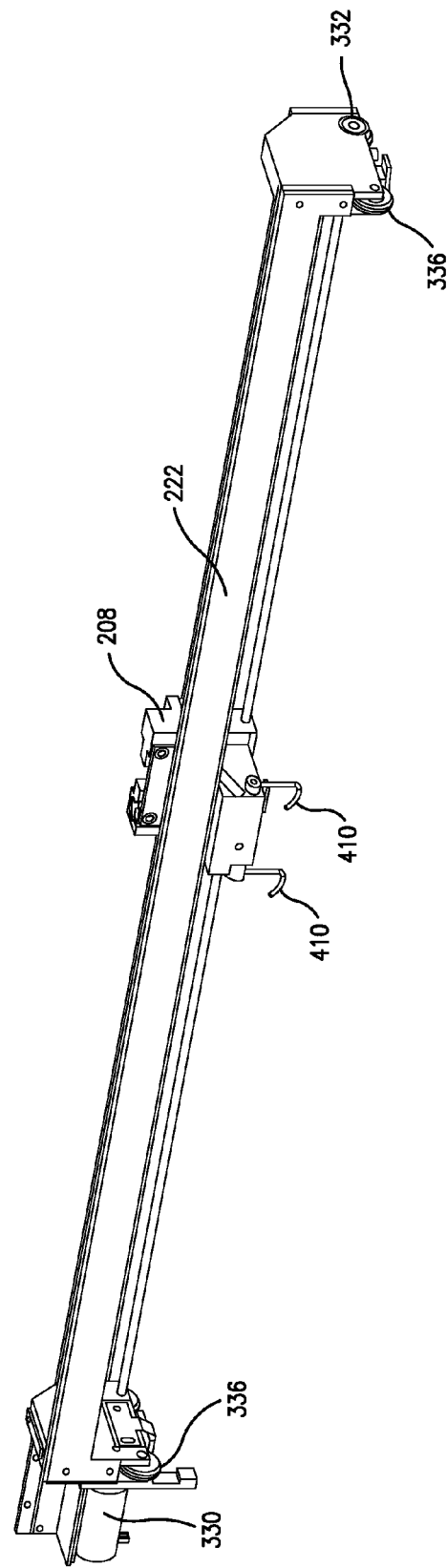
FIG. 9 is a rear perspective view of the carriage and the shuttle assembly of the dispensing unit of FIG. 1.

With reference to FIGS. 8 and 9, the X-axis support 222 is configured to receive the shuttle assembly 208. As shown in FIG. 6, the shuttle assembly 208 includes an X-axis drive motor 314 to provide movement to the shuttle assembly 208 relative to the X-axis support 222. To provide such movement, the shuttle assembly 208 may utilize a pinion 315 coupled to the X-axis drive motor 314 to drivably engage a rack (not shown) fixed to the X-axis support 222. As such, rotation of the pinion 315 may cause the shuttle assembly 208 to move from side to side in the housing 102. The X-axis drive motor 314 may interface with a controller 128, which may selectively activate the X-axis drive motor 314 when prompted by the computer 124. The shuttle assembly 208 may also include a plurality of roller bearings 316 (see also FIG. 7) to engage one or more surfaces of the X-axis support 222 to secure the shuttle assembly 208 in the X-axis support 222. Alternatively, other known drive structure may be utilized to move the shuttle assembly 208 relative to the X-axis support 222.

With reference to FIGS. 6 and 7, the shuttle assembly 208 also includes a positioning system or an "overtravel" system to detect the proximity of the shuttle assembly 208 to opposite end walls 318 of the X-axis support 222 (see FIG. 8). Such an overtravel system may interface with the controller 128 and the computer 124 to substantially prevent the shuttle assembly 208 from impacting the end walls 318 of the X-axis support 222. More particularly, as shown in FIGS. 6 and 7, the overtravel system includes an activation rod 320 slidably supported in the shuttle assembly 208. The activation rod 320 is biased toward a central position by springs 322 on opposite sides of the shuttle assembly 208. The activation rod 320 includes cam surfaces 324 that are engageable by respective followers 326 coupled to respective overtravel switches 328.

During operation, the activation rod 320 may contact one of the end walls 318 of the X-axis support 222 to move the rod 320 from its biased central position. Depending on which end wall 318 is contacted, one of the springs 322 is compressed to gently slow down the shuttle assembly 208. As the rod 320 is moved, one of the followers 326 is engaged by the corresponding cam surface 324 on the rod 320 to trigger the corresponding overtravel switch 328. Furthermore, the overtravel switches 328 interface with the controller 128 and the computer 124 to alert the computer 124 when the shuttle assembly 208 is in close proximity to one of the end walls 318 of the X-axis support 222 to de-activate or stop the X-axis drive motor 314. Alternatively, the overtravel system may be configured with non-contact switches (e.g., light switches, magnetic switches, etc.) During impact, the springs 322 also absorb at least a portion of the impact energy to substantially prevent damage to the shuttle assembly 208.

With reference to FIGS. 8 and 9, the X-axis support 222 includes a Z-axis drive motor 330. Like the X-axis drive motor 314, the Z-axis drive motor 330 may drive one or more pinions 332 via a drivetrain (not shown), such that the pinions 332 engage a rack 334 fixed to one of the Z-axis supports 204 (see FIG. 10). As such, rotation of the pinions 332 may cause the X-axis support 222 to move from the front of the housing 102 to the rear of the housing 102. The Z-axis drive motor 330 may interface with the controller 128, which may selectively activate the Z-axis drive motor 330 when prompted by the computer 124. The X-axis support 222 may also include a plurality of rollers 336 to engage one or more surfaces of the Z-axis supports 204 to facilitate substantially smooth movement of the X-axis support 222 over the Z-axis supports 204. Alternatively, other known drive structure may be utilized to move the X-axis support 222 relative to the Z-axis supports 204.

Figure 10:
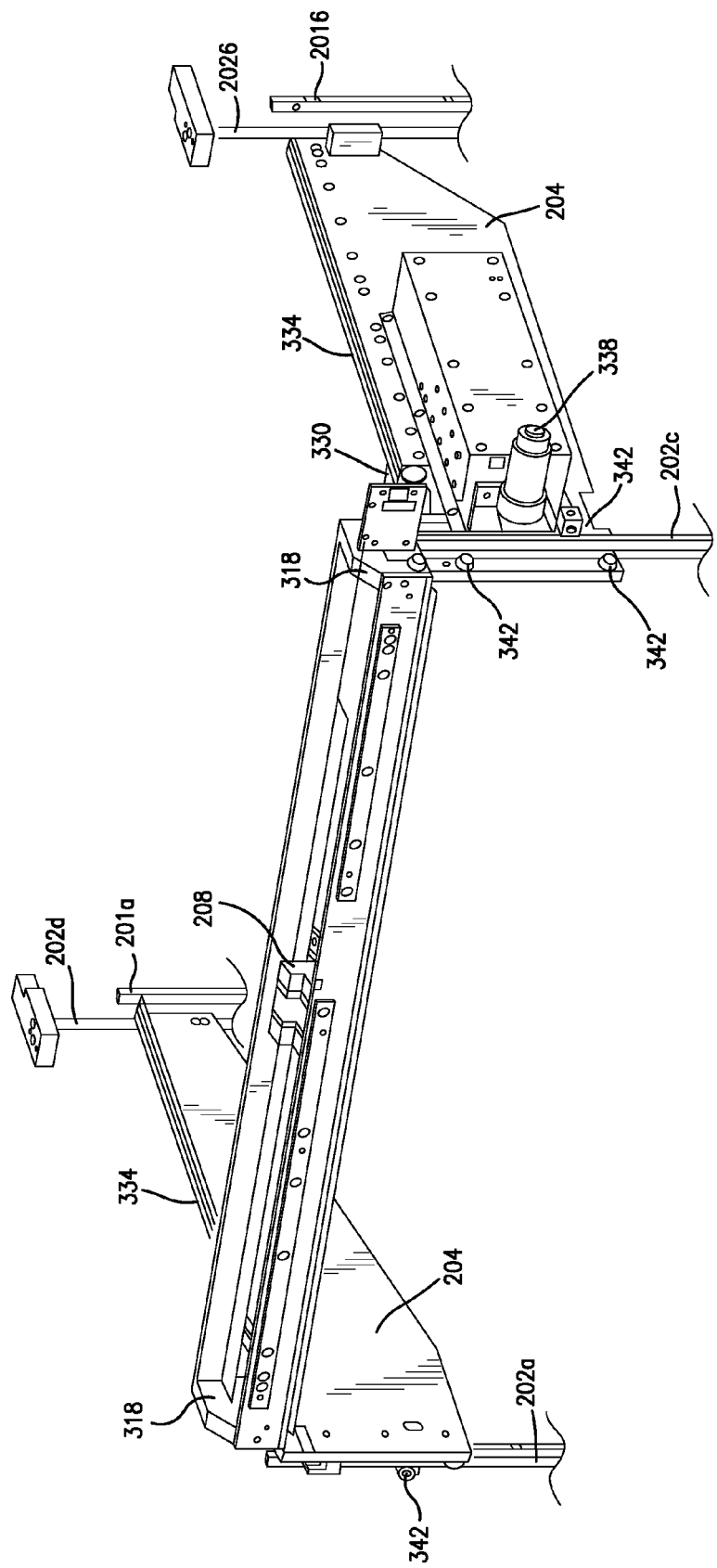
FIG. 10 is a top perspective view of the carriage and shuttle assembly of FIG. 8 supported by a Z-axis support.

With reference to FIG. 10, one of the Z-axis supports 204 includes a Y-axis drive motor 338. The Z-axis supports 204 may also be structurally interconnected by one or more crossmembers (not shown) such that only one Y-axis drive motor 338 is sufficient. Alternatively, both Z-axis supports 204 may include respective Y-axis drive motors 338 that are synchronized. Like the X-axis drive motor 314 and the Z-axis drive motor 330, the Y-axis drive motor 338 may include a pinion (not shown) coupled thereto to drivably engage a rack (not shown) fixed to one of the Y-axis supports 202a-202d. Alternatively, a multiple-gear gear train may be utilized between the pinion and the rack. As such, rotation of the pinion may cause the Z-axis supports 204 to move from the top of the housing 102 to the bottom of the housing 102. The Y-axis drive motor 338 may interface with the controller 128, which may selectively activate the Y-axis drive motor 338 when prompted by the computer 124. The Z-axis supports 204 may also include a plurality of roller bearings 342 to engage one or more surfaces of the Y-axis supports 202a-202d to facilitate substantially smooth movement of the Z-axis supports 204 over the Y-axis supports 202a-202d. Alternatively, other known drive structure may be utilized to move the Z-axis supports 204 relative to the Y-axis supports 202a-202d.

Figure 17:
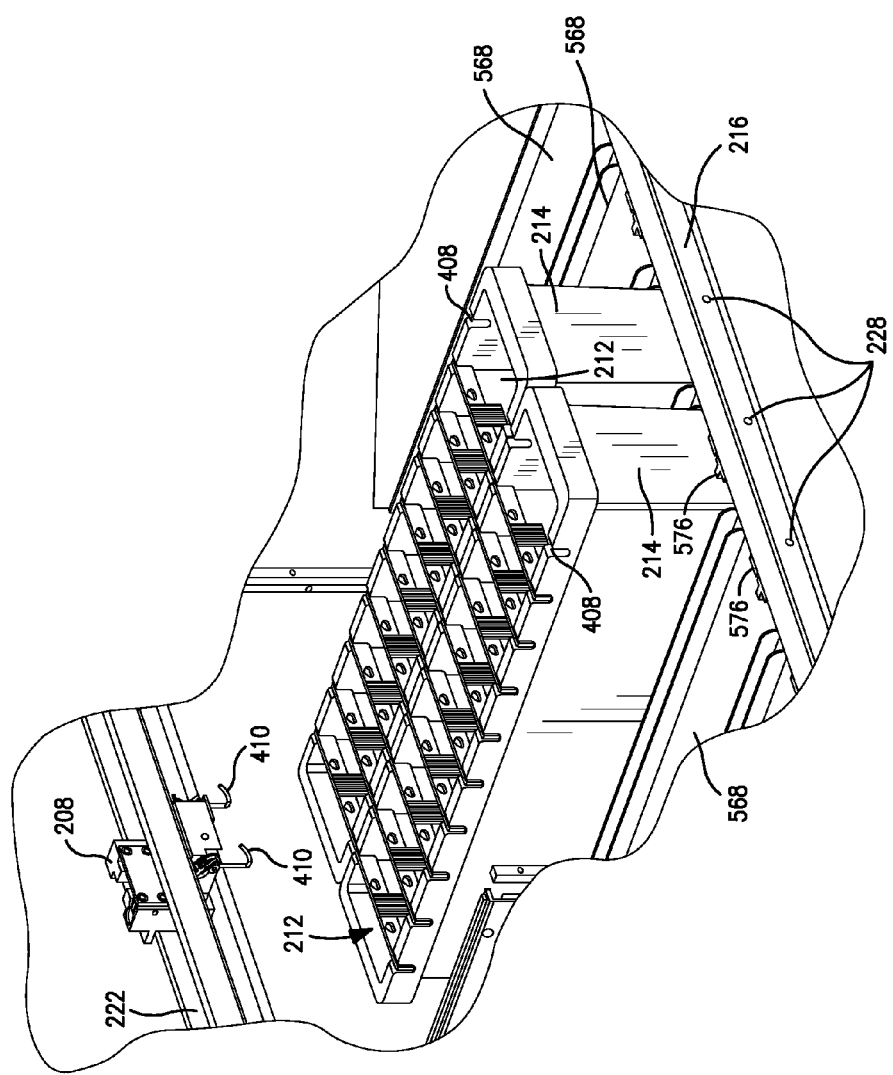
FIG. 17 is a rear perspective view of the dispensing unit of FIG. 1, illustrating a plurality of distribution trays and the shuttle assembly.
Figure 23:
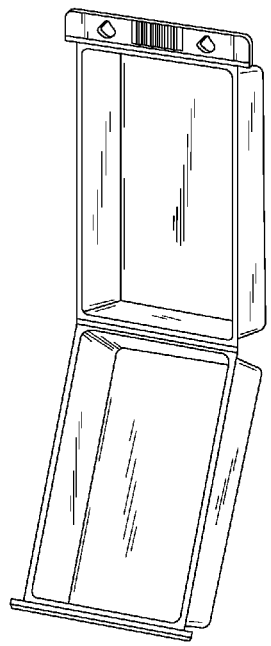
FIG. 23 is a front perspective view of yet another construction of a bag or container for storing the finished prescriptions.

As shown in FIG. 17, a plurality of prescription bags 212 are stored in a plurality of distribution bins or trays 214, which, in turn, are supported by the plurality of platforms 216. The prescription bags 212 may include one or more finished prescriptions or containers 902 (see FIGS. 18 and 20) therein for packaging the prescription drugs. Further, instead of bags 212, other types of containers (e.g., clamshell-type containers, see FIG. 23) may be stored directly in the trays 214. Like reference numerals will be used to describe like components.

Figure 21:
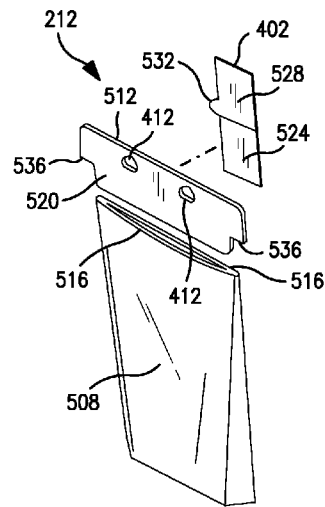
FIG. 21 is an exploded, front perspective view of another construction of a bag or container for storing the finished prescriptions.
Figure 22:
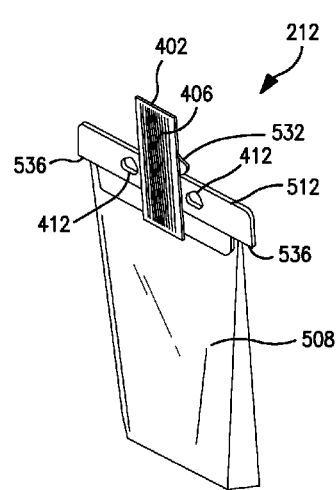
FIG. 22 is an assembled, rear perspective view of the bag or container of FIG. 21.

FIGS. 21-22 illustrate one construction of the prescription bags 212. Generally, each bag 212 includes a receptacle 508, in which the filled prescriptions or other products are positioned, and a header 512, which couples to the receptacle 508 and provides apertures 412 through which hooks 410 (described below in greater detail) of the shuttle assembly 208 are inserted to pick the prescription bag 212. In the illustrated construction, the prescription bag 212 is assembled from separate components. However, in alternate constructions of the bag 212, the receptacle 508 and the header 512 may be integrally formed with one another e.g., in the clamshell-type container of FIG. 23).

As shown in FIG. 21, the receptacle 512 includes opposite side walls 516 defining an open end of the receptacle 508. During assembly of the bag 212, an insertion portion 520 of the header 512 is inserted into the open end of the receptacle 508. The header 512 and the receptacle 508 may be made from similar plastic materials and heat-staked or heat-sealed to one another. Then, a label 402 having a barcode 406 printed thereon is coupled to one side of the header 512 and to one of the side walls 516 of the receptacle 508 (see FIG. 22). More particularly, the label 402 includes an adhesive substance 524 on one side thereof to couple to the header 512 and the receptacle 508. A removable backing 528 is joined to a portion of the side of the label 402 having the adhesive substance 524. The backing 528 includes a tab 532 to facilitate removal of the backing 528 from the label 402. The portion of the label 402 with the backing 528 extends beyond an outer periphery of the header 512.

The assembled bag 212, as illustrated in FIG. 22, is ready to receive a filled prescription therein. After receiving a filled prescription, the backing 528 may be removed from the label 402, and the label 402 may be folded over the header 512 and secured to the other side of the header 512 and the other side wall of the receptacle 508 to close the open end of the receptacle 508. The apertures 412 are configured with an apex, such that the header 512 is accurately and precisely oriented with respect to the hooks 410 of the shuttle assembly 208 when the prescription bag 212 is picked. Alternatively, the apertures 412 may be configured with other shapes at least partially defining an apex (e.g., a diamond, a pentagon, etc.), or the apertures 412 may be circular-shaped.

The headers 512 of the bags 212 include opposing alignment tabs 536 that engage slots formed in the trays 214 to maintain consistent spacing between adjacent headers 512 of adjacent bags 212. Also, the alignment tabs 536 facilitate reading of the barcodes 406 on the labels 402 by consistently positioning the labels 402 so they are clearly presented to the barcode reader 210.

Figure 20:
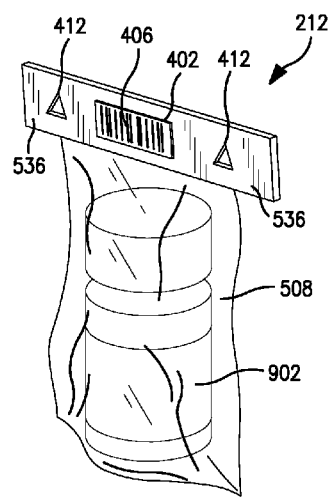
FIG. 20 is a perspective view of a first construction of a bag or container for storing the finished prescriptions.

FIG. 20 illustrates an alternative construction of the bag 212, in which paper or cardboard headers 512 may be used. The labels 402 may be printed to the headers 512, and alternative methods may be used to close the receptacle 508.

As shown in FIGS. 4 and 5, the platforms 216 are movable in relation to each other so that a higher density of platforms 216, distribution trays 214, and prescription bags 212 can be stored in the housing 102. Except for the lower-most platform 216 that remains stationary, each platform 216 includes means to raise and lower the platform 216 (e.g., gear motor 220), thereby allowing the shuttle assembly 208 to reach a specific prescription bag 212 stored in a specific distribution tray 214.

With reference to FIG. 5, a staging area 302 toward the front of the housing 102 is shown. The staging area 302 allows a working space for the shuttle assembly 208 to be positioned or stored while the platforms 216 are being moved in anticipation of accessing a particular prescription bag 212. In addition, the staging area 302 provides the working area in which the shuttle assembly 208 delivers the selected prescription bag 212 to the dispense bin 310.

The gear motor 220 may include a pinion (not shown) to drivably engage a rack (also not shown) on the platform support 210b. The rack utilized by the platforms 216 is separate and distinct from the rack utilized by the Z-axis supports 204, such that the platforms 216 and the Z-axis supports 204 may move without affecting one another. Alternatively, a single motor or gear motor may be utilized to raise and lower all of the platforms 216. In addition, hydraulic motors or pneumatic motors may be utilized in place of or in addition to the electric motors 220.

With reference to FIG. 7, the shuttle assembly 208 includes a barcode reader 210 for reading the barcodes 406 (see FIG. 22) on the prescription bags 212. In this way, the shuttle assembly 208 has the capability to associate a specific prescription bag 212 with a random storage location in the housing 102. The shuttle assembly 208 may also include a bag sensor 540 configured to detect the presence of a prescription bag 212 in a specific slot in a tray 214. The bag sensor 540 may be utilized in combination with the barcode reader 210, such that the bag sensor 540 may first detect whether or not a prescription bag 212 is located in a specific slot in a tray 214 before the barcode reader 210 attempts to scan the barcode 406 of the bag 212. If a prescription bag 212 is not detected in a particular slot in the tray 214 by the bag sensor 540, then an attempt to scan the barcode 406 of the missing bag 212 is not made by the barcode reader 210. This may allow for a more expedient process when inventorying the bags 212 in the unit 100, which is discussed in more detail below.

The barcode reader 210 is operable to interface with the computer 124 to output the locations of the individual bags 212 to a database program in the computer 124. The database program thus provides an inventory of the prescription bags 212 stored in the unit 100. When it is desired to access a selected prescription bag 212, the controller 128 interfaces with the computer 124, the gear motors 220 to control movement of the platforms 216, and the drive motors 314, 330, 338 to control movement of the shuttle assembly 208, the X-axis support 222, and the Z-axis supports 204 to position the shuttle assembly 208 in a defined location within the housing 102. In addition, the controller 128 may interface with a hook motor 364 in the shuttle assembly 208 to maneuver hooks 410 to pick a selected prescription bag 212, which is discussed in more detail below. Although the controller 128 is shown as a separate component from the computer 124, it will be understood by those of ordinary skill in the art that the controller 128 and the computer 124 may be incorporated into a single component.

FIG. 5 illustrates the shuttle assembly 208 delivering a selected prescription bag 212 to the dispense bin 310 for delivering the prescription bag 212 to a specific customer. The selected prescription bag 212 originated from a random slot in a random distribution tray 214 located toward the upper portion of the housing 102. Upon identification of the customer, the computer 124 queried the database program to ascertain the location of the selected prescription bag 212. When the location of the prescription bag 212 was determined, the controller 128 interfaced with the lifting mechanism or gear motors 220 to raise the top two platforms 216 to allow access to the distribution tray 214 containing the selected prescription bag 212. The controller 128 then interfaced with the drive motors 314, 330, 338 to maneuver the shuttle assembly 208 into place to select the prescription bag 212. Further, the controller interfaced with the hook motor 364 to maneuver the hooks 410 through respective apertures 412 in the bag 212 to pick the prescription bag 212. Alternatively, more than one shuttle assembly 208 may be used in the unit 100 to expedite retrieving more than one prescription bag 212.

To dispense the selected prescription bag 212, the shuttle assembly 208 is advanced toward the front of the housing 102 along the Z-axis 116, lowered along the Y-axis 112 to a position above the distribution tray 214, then moved along the X-axis 120 to position the prescription bag 212 directly above the deployed dispense bin 310, the operation of which is described in more detail below. The hook motor 364 is then activated to maneuver the hooks 410 to drop the prescription bag 212 into the dispense bin 310.

Figure 11:
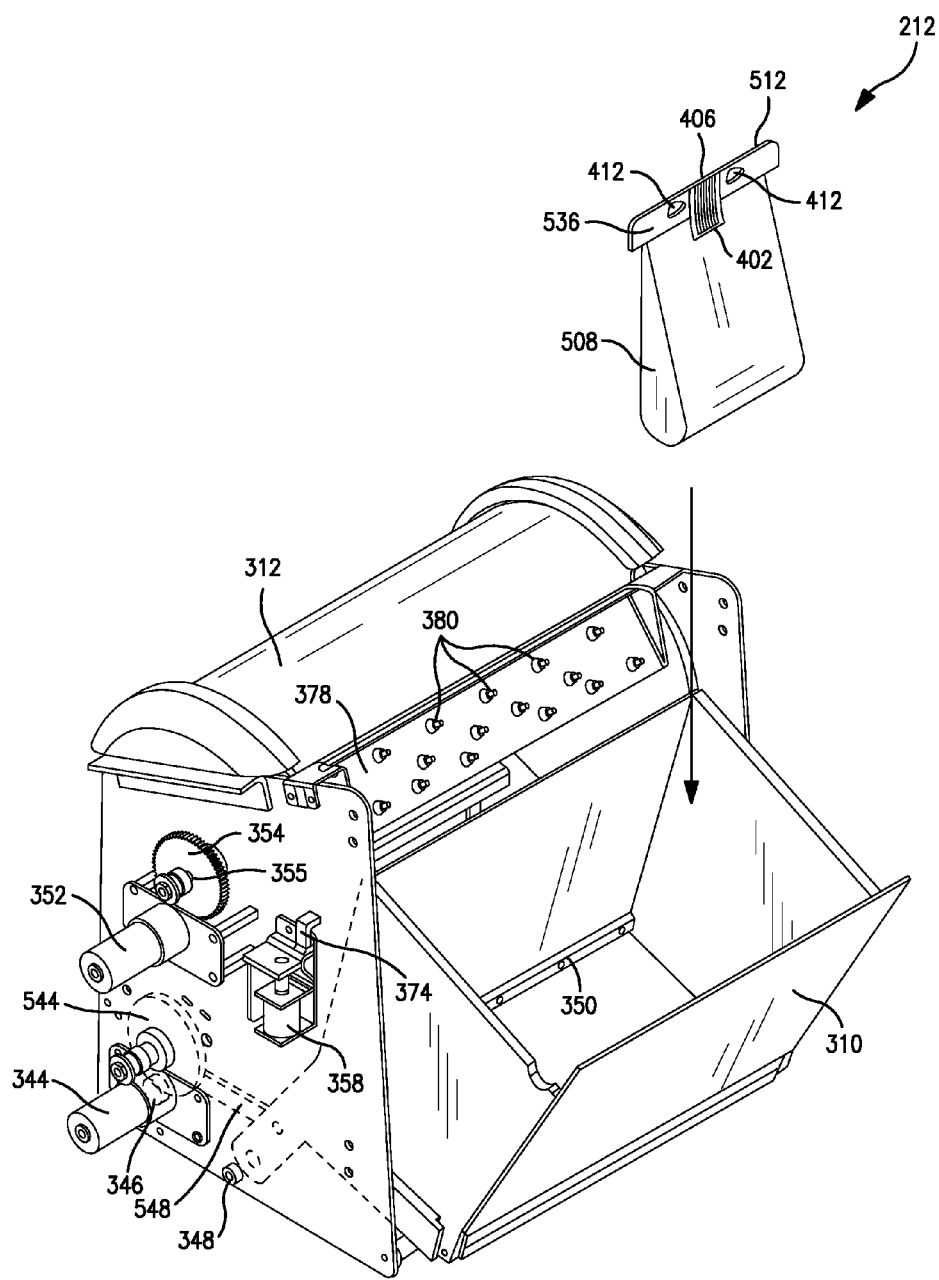
FIG. 11 is a rear perspective view of a dispense bin of the dispensing unit of FIG. 1, illustrating the dispense bin being deployed to receive a finished prescription.

The dispense bin 310 is illustrated in more detail in FIGS. 11-16. With reference to FIG. 11, the dispense bin 310 is movable between a deployed position, in which the prescription bag 212 may be dropped into the dispense bin 310, and a non-deployed position (see FIG. 13), in which the prescription bag 212 is accessible to the customer for removal. More particularly, as shown in FIG. 11, the dispense bin 310 is pivotable between its deployed and non-deployed positions by a drive train. A dispense bin drive motor 344 may include a pinion 346 coupled thereto to drivably engage a driven gear 544. A link 548 may be rotatably coupled at one end to the driven gear a distance from the rotational axis of the driven gear 544. The link 548 may also be rotatably coupled at an opposite end to the dispense bin 310 a distance from a pivot point 348 of the dispense bin 310. As such, the driven gear 544, link 548, and the dispense bin 310 effectively function as a crank-rocker mechanism in that rotation of the driven gear 544 causes the dispense bin 310 to pivot about its pivot point 348 between its deployed and non-deployed positions.

Alternatively, other drive trains may be utilized, including fixing the driven gear to the pivot point 348 of the dispense bin 310, such that the pinion 346 engages the driven gear and causes the dispense bin 310 to pivot without utilizing the link 548. Alternatively, a multiple-gear gear train may be utilized between the pinion 346 and the driven gear on the dispense bin 310. Further, other known drive structures may be utilized to pivot the dispense bin 310 between its deployed and non-deployed positions. A slip-clutch 349 may also be utilized in the drive train of the dispense bin 310 to allow selective slippage between the motor 344 and the dispense bin 310.

The dispense bin drive motor 344 may interface with the controller 128, which may selectively activate the dispense bin drive motor 344 when prompted by the computer 124. With reference to FIG. 11, a product sensor 350 may be positioned in the dispense bin 310 to detect the presence or absence of a prescription bag 212. The product sensor 350 may interface with the computer 124 and the controller 128 to indicate the presence or absence of a prescription bag 212 in the dispense bin 310. In the illustrated configuration, the product sensor 350 is a light sensor. An illumination bar 378 containing a plurality of illumination devices 380 (e.g., light emitting diodes, incandescent lights, and so forth) may be positioned above the dispense bin 310 when the dispense bin 310 is in its non-deployed position. The computer 124 may prompt the controller 128 to activate the illumination devices 380 when a prescription bag 212 is dispensed into the dispense bin 310 for the customers convenience in retrieving the prescription bag 212 from the dispense bin 310. In addition, if the product sensor 350 detects that the prescription bag 212 has not been removed by the customer after a period of time, the controller 128 may cause the illumination devices 380 to flash to alert the customer to remove the prescription bag 212 from the dispense bin 310.

Figure 12:
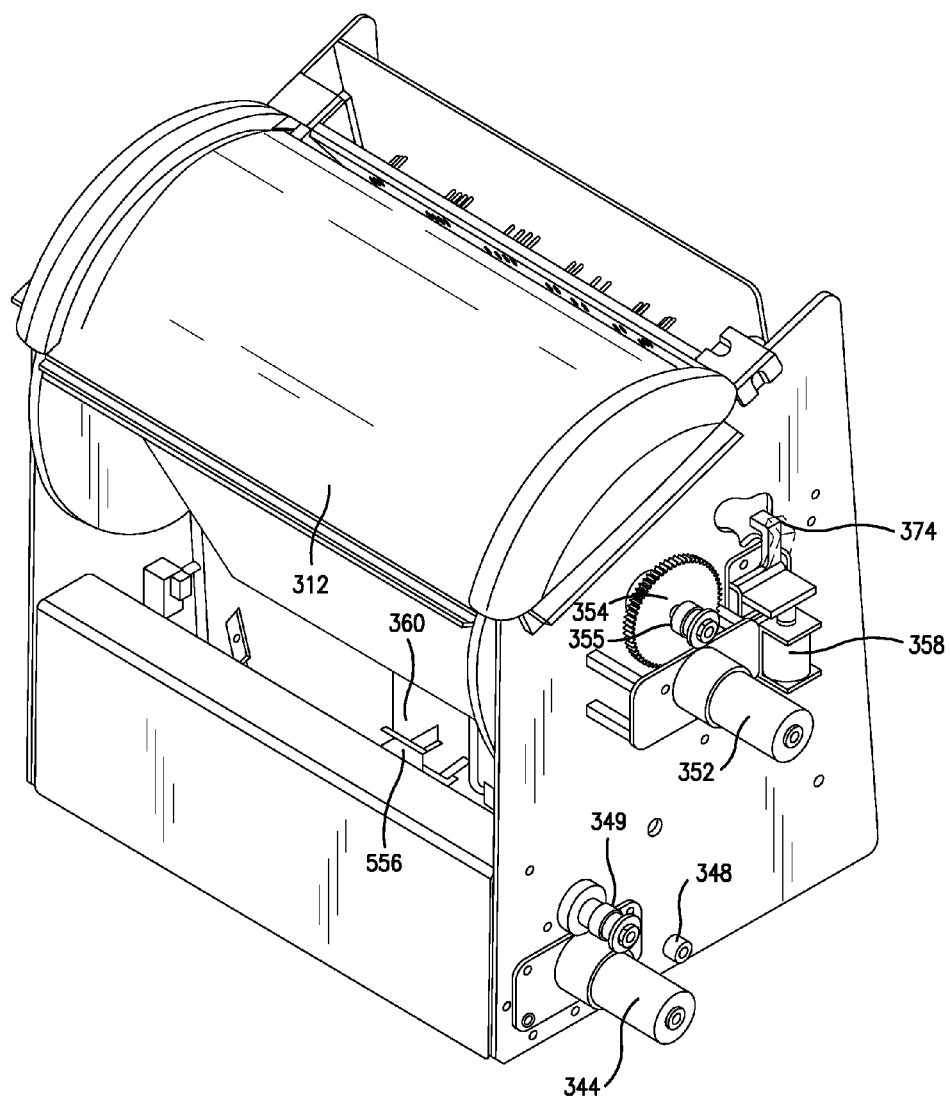
FIG. 12 is a front perspective view of the dispense bin of FIG. 11, illustrating a dispense bin lid in a closed position.
Figure 13:
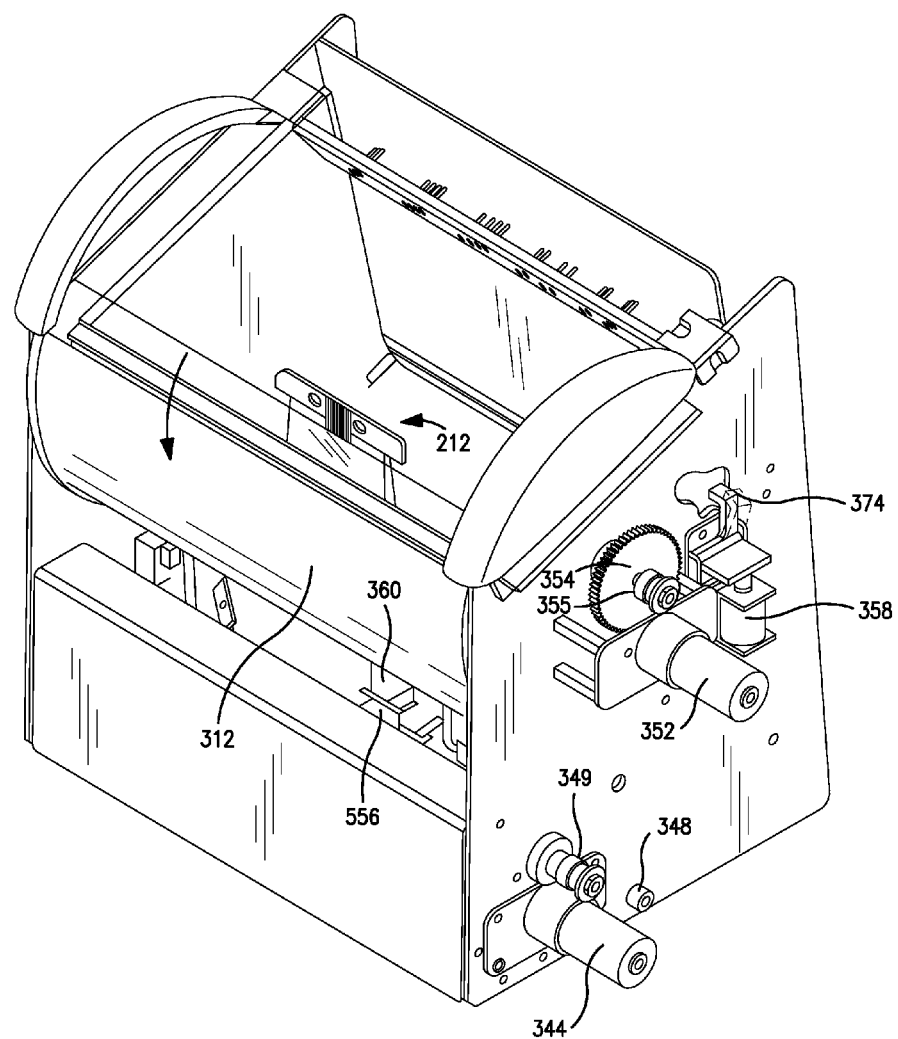
FIG. 13 is a front perspective view of the dispense bin of FIG. 11, illustrating the dispense bin lid in an open position so the finished prescription may be removed from the dispense bin.

With reference to FIGS. 12 and 13, the dispense bin lid 312 is movable between a closed position (see FIG. 12), in which the prescription bag 212 is inaccessible to the customer, and an open position (see FIG. 13), in which the prescription bag 212 is accessible to the customer for removal. More particularly, as shown in FIG. 12, the dispense bin lid 312 is pivotable between its closed and open positions by a drive train. A dispense bin lid drive motor 352 may include a pinion 353 (see FIG. 14) coupled thereto to drivably engage a driven gear 354 fixed to the dispense bin lid 312 at the pivot point of the dispense bin lid 312. As such, rotation of the pinion 353 may cause the dispense bin lid 312 to pivot between its closed and open positions. Alternatively, a multiple-gear gear train may be utilized between the pinion 353 and the driven, gear 354 on the dispense bin lid 312. The dispense bin lid drive motor 352 may interface with the controller 128, which may selectively activate the dispense bin lid drive motor 352 when prompted by the computer 124. Alternatively, other known drive structures may be utilized to pivot the dispense bin lid 312 between its closed and open positions. A slip-clutch 355 may also be utilized in the drive train of the dispense bin lid 312 to allow selective slippage between the motor 352 and the dispense bin lid 312.

With reference to FIG. 12, the dispense bin lid 312 may be locked in its closed position by a solenoid 358 actuating a lock mechanism 374. The lock mechanism 374 is biased to engage an aperture 572 in the dispense bin lid 312. A switch 376 (see FIG. 15) may be used in combination with the computer 124 to detect whether the lock mechanism 374 is engaged with the dispense bin lid 312 to lock the dispense bin lid 312, or disengaged from the dispense bin lid 312 to unlock the dispense bin lid 312.

With reference to FIG. 13, the dispense bin lid 312 is shown in the open position to allow the customer to remove the prescription bag 212 from the dispense bin 310. If, however, the prescription bag 212 is not removed from the dispense bin 310 after a predetermined period, the dispense bin lid 312 may be closed to prevent unintended disbursement of the prescription bag 212 to the wrong customer. The product sensor 350 may be utilized to detect whether or not the prescription bag 212 is removed from the dispense bin 310, and the product sensor 350 may interface with the controller 128 and the computer 124 to activate the dispense bin lid drive motor 352 to close the dispense bin lid 312.

Figure 14:
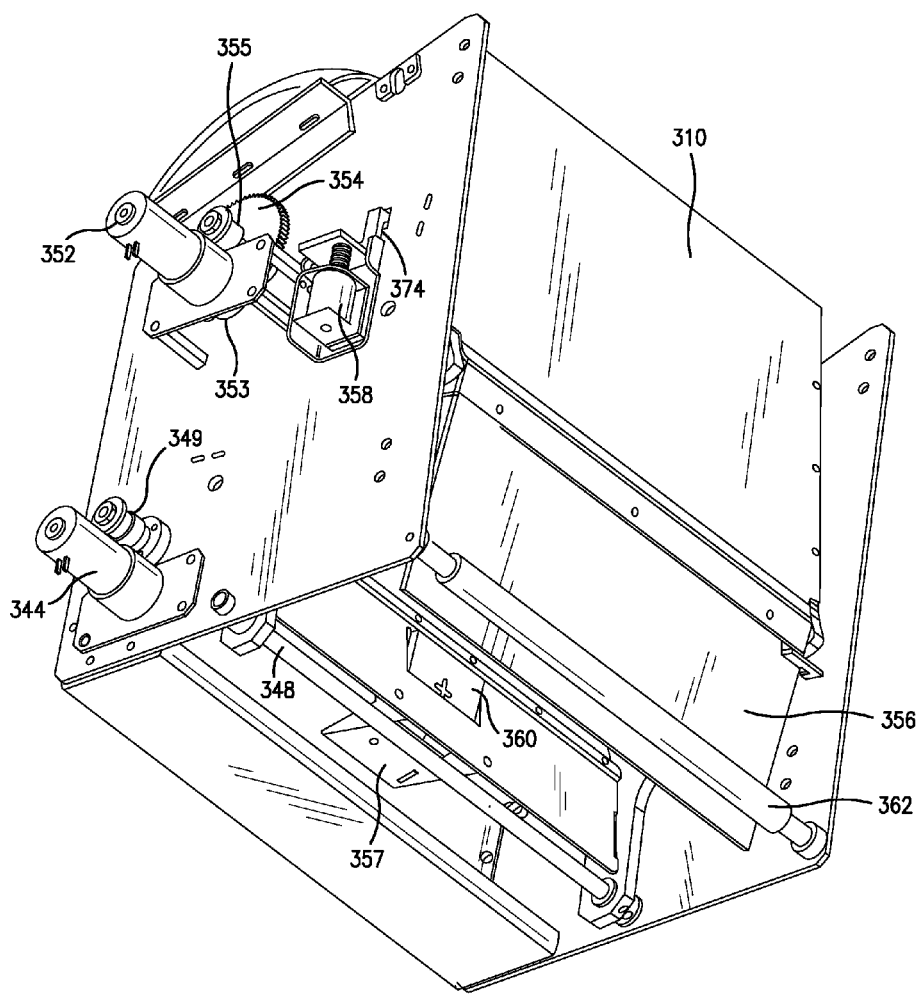
FIG. 14 is a rear perspective view of the dispense bin of FIG. 11, illustrating a trap door being deployed to drop the finished prescription from the dispense bin.

With reference to FIG. 14, the dispense bin 310 may also incorporate a trap door 356 to allow the prescription bag 212 left in the dispense bin 310 to be dropped from the dispense bin 310 into a return bin 552. The prescription bags 212 dropped into the return bin 552 may then be re-checked by the pharmacist or technician and returned to a distribution tray 214 in the unit 100. In the illustrated construction, the return bin 552 is supported below the dispense bin 310 in the access door 313. The pharmacist or technician may periodically check the return bin 552 by opening the access door 313 and removing the return bin 552. The prescription bags 212 in the return bin 552 may then be reloaded into the unit 100 as described in more detail below.

The trap door 356 is actuated by a solenoid 556 (see FIGS. 12 and 13) and a spring-biased latch mechanism 360. The solenoid is mounted on a bracket 357 (see FIG. 14) coupled to the dispense bin 310. The solenoid may interface with the controller 128, which may selectively activate the solenoid when prompted by the computer 124. FIG. 14 illustrates the trap door 356 in a deployed position, in which the prescription bag 212 is allowed to drop from the dispense bin 310 and into the return bin 552. To deploy the trap door 356, the controller 128 activates the solenoid, which, in turn, retracts the spring-biased latch mechanism. The mechanism 360 is sufficiently retracted by the solenoid to allow the trap door 356 to pivot downwardly to its deployed position.

Figure 15:
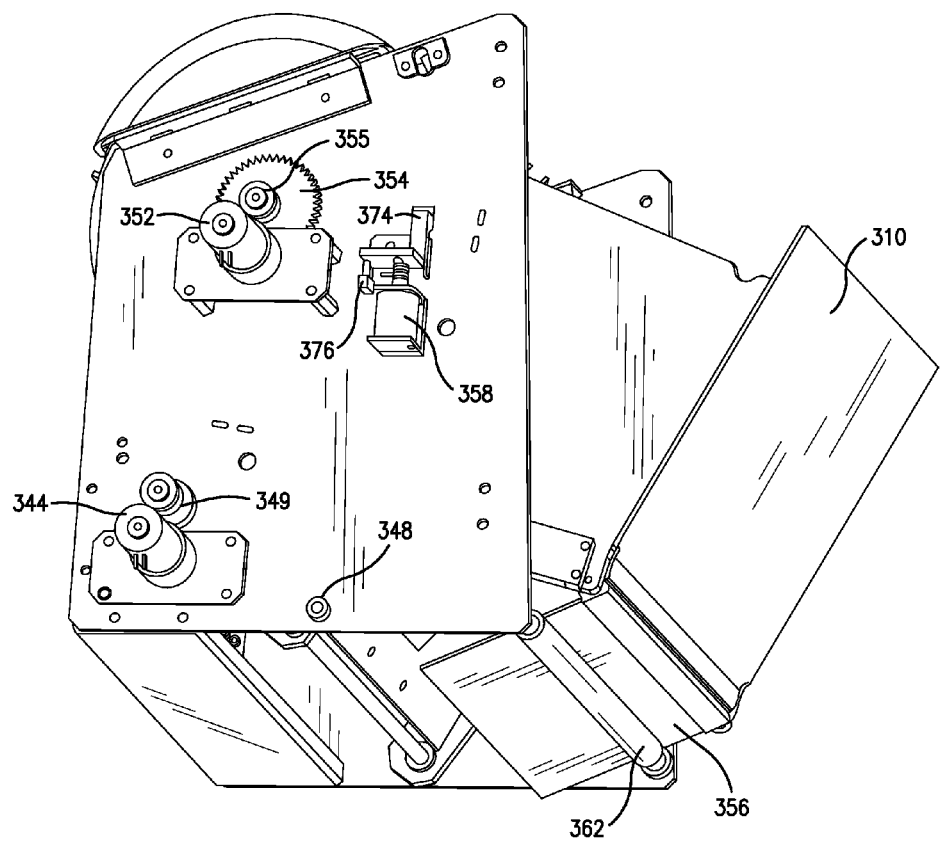
FIG. 15 is a rear perspective view of the dispense bin of FIG. 11, illustrating the trap door being moved to a closed or non-deployed position.
Figure 16:
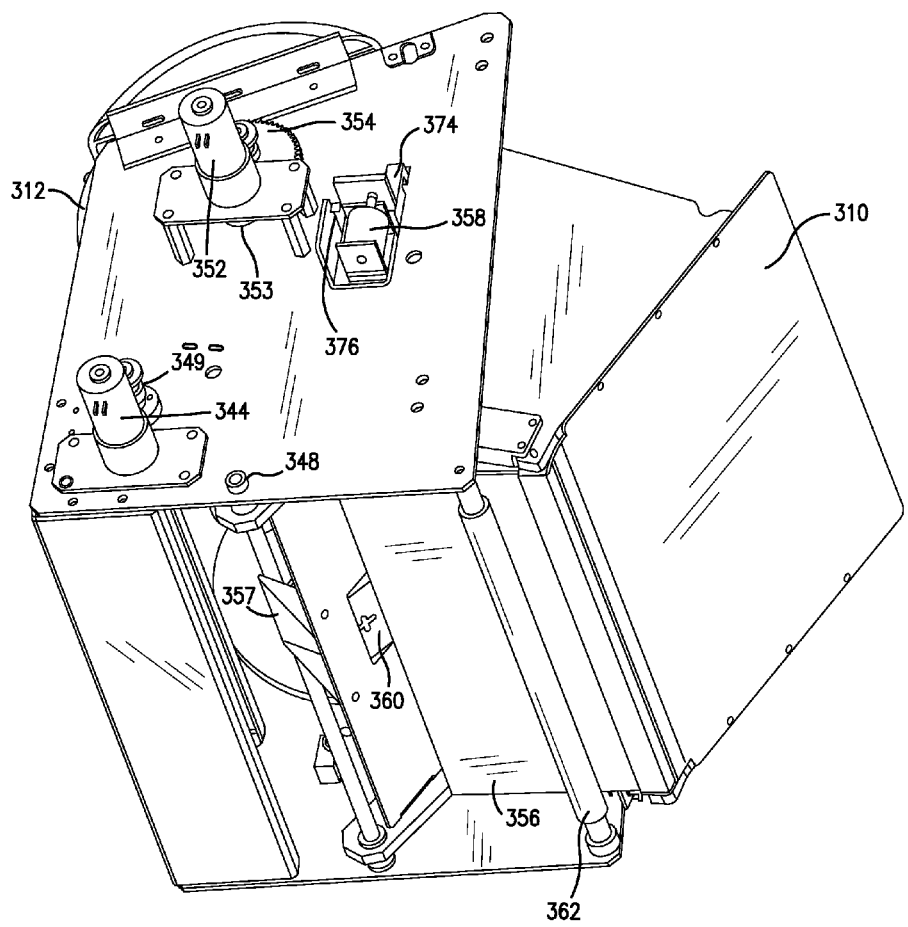
FIG. 16 is a rear perspective view of the dispense bin of FIG. 11, illustrating continued movement of the trap door toward its closed or non-deployed position.

With reference to FIGS. 15 and 16, after the prescription bag 212 is dropped from the dispense bin 310, the trap door 356 is moved to its closed or non-deployed position. To accomplish this, the dispense bin drive motor 344 is activated to pivot the dispense bin 310 to its deployed position. While the dispense bin 310 deploys, the trap door 356 contacts a stationary bar 362 spaced from the dispense bin 310. Continued pivoting of the dispense bin 310 causes the trap door 356 to pivot relative to the dispense bin 310. As shown in FIG. 16, before the dispense bin 310 reaches its deployed position, the trap door 356 engages the latch mechanism 360 and causes the latch mechanism 360 to retract against its spring bias until the trap door 356 clears the latch mechanism 360, at which time the latch mechanism 360 springs outwardly to secure the trap door 356 in its closed or non-deployed position.

More than one dispense bin 310 or pickup location may be incorporated into the unit 100 if it is desired to service more than one customer at a given time. Further, additional shuttle assemblies 208 may be incorporated into the unit 100 to service the additional customers or to pick multiple prescription bags 212 at one time. The unit 100 may also be configured as a double-wide or a triple-wide unit (not shown), such that two or three of the illustrated storage units 100 may be incorporated into a single housing. In such a double-wide or triple-wide unit, one or more transfer mechanisms (e.g., conveyor belts, etc.) may be utilized to transfer a prescription bag 212 between the individual storage units 100 in the double-wide or triple-wide units. For example, a shuttle assembly 208 of a first unit 100 may deposit a prescription bag 212 on the conveyor belt, which may transport the bag 212 to a second unit 100 in the double-wide or triple-wide unit. The conveyor belt may then drop the bag 212 directly into the dispense bin 310 of the second unit 100.

Figure 28:
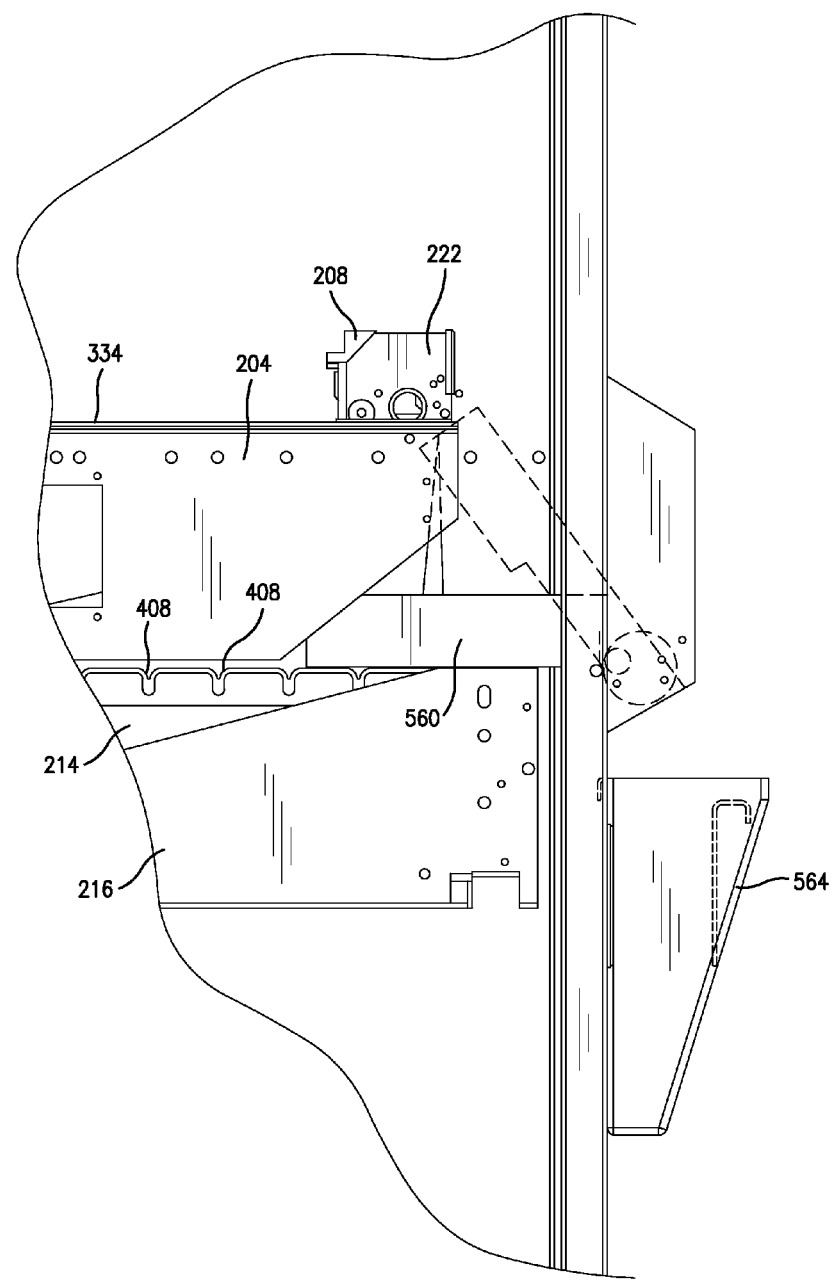
FIG. 28 is a partial cutaway view of the dispensing unit of FIG. 1, illustrating rear dispense of a finished prescription.

With reference to FIG. 28, the shuttle assembly 208 may also deliver the prescription bag 212 to the rear of the housing 102 for the bag 212 to be dispensed from the rear of the housing 102. This may be desirable when the pharmacist or technician wants to access one particular prescription bag 212 in the housing 102, rather than manually accessing a particular tray 214 in the housing. A chute 560 may be located in the housing 102 and pivotable with respect to the housing 102 about a substantially horizontal axis. The chute 560 may be pivotable between a substantially horizontal position, in which the chute 5650 may receive the prescription bag 212 from the shuttle assembly 208, and a substantially vertical position, in which the bag 212 may slide down the chute 560 for deposit in a bin 564. The bin 564 may be removably coupled to the housing 102, such that the pharmacist or technician may detach the bin 564 from the housing 102 to transport the dispensed bags 212.

FIG. 17 illustrates a close-up view of the shuttle assembly 208 reading, identifying, and selecting a particular prescription bag 212 from a particular distribution tray 214. The shuttle assembly 208 utilizes its barcode reader 210 to read the barcode 406 on the label 402 that is located on the prescription bag 212. Alternatively, various forms of electronic identification tags containing information relevant to the customer and/or the prescription may be applied to the prescription bag 212. Accordingly, a means to read these tags may be used in place of the barcode reader 210.

The prescription bag 212 may include labels 402 on each side of the bag 212, such that the barcode reader 210 may read the barcode 406 to identify the bag 212 from either side of the bag 212 by reference or query of the database. The distribution trays 214 include self-aligning V-notches 408 so that the label 402 of each bag is accurately positioned in the distribution tray 214 to facilitate reading of the barcodes 406 by the barcode reader 210.

As shown in FIGS. 6 and 7, the shuttle assembly 208 includes a mechanism (e.g., hooks 410) for engaging corresponding openings or apertures 412 in the prescription bag 212 to remove the prescription bag 212 from the tray 214. With reference to FIG. 6, the hooks 410 are fixed to a single shaft (not shown) passing through the shuttle assembly 208. A hook drive motor 364 includes a pinion 366 coupled thereto to drivably engage a driven gear 368 fixed to the common shaft of the hooks 410. As such, rotation of the pinion 366 causes the hooks 410 to pivot about their common shaft between an "up" or raised position, and a "down" or lowered position. The hook drive motor 364 may interface with the controller 128, which may selectively activate the hook drive motor 364 when prompted by the computer 124. Alternatively, a multiple-gear gear train may be utilized between the pinion 366 and the driven gear 368 on the common shaft of the hooks 410. Further, other known drive structures may be utilized to pivot the hooks 410 between their up and down positions.

One or more switches 370 may be utilized to detect the position of the hooks 410. As shown in FIGS. 6 and 7, one switch 370 may be utilized to detect the up position of the hooks 410, while a second switch 370 may be utilized to detect the down position of the hooks 410. The switches 370 may interface with the controller 128 and the computer 124 to determine when to deactivate the hook drive motor 364.

The hooks 410 may be maneuvered to disengage the apertures 412 in the prescription bag 212 when the prescription bag 212 is to be dropped into the dispense bin 310. Alternatively, the shuttle assembly 208 may utilize different means for selecting the prescription bags 212, such as, for example, suction, magnets, grabbers, holders, and so forth. As such, the prescription bags 212 may incorporate corresponding structure or features, depending upon the different means for selecting the prescription bags 212, to allow accurate and precise picking of the prescription bags 212. For example, grabbers are particularly suited to pick products having a consistent shape and size (e.g., DVD's). Further, such products may not require bags or other containers for vending, and may be directly grasped by the grabbers.

FIG. 2 illustrates the rear of housing 102, which is accessed when the unit 100 is to be reloaded with additional prescription bags 212. Alternatively, the access door 313 may be opened to allow the housing 102 to be accessed from the front for reloading.

The housing 102 may include one or more rear doors 602, which may be locked by electronic solenoids (not shown). The electronic solenoids may be controlled by the computer 124 and the controller 128 to lock and unlock the rear doors 602. The pharmacist or technician may utilize another computer (e.g., the computer or computer network in the pharmacy) to interface with the computer 124 to remotely actuate the electronic solenoids to lock or unlock the rear doors 602. Alternatively, the pharmacist or technician may utilize a keypad (not shown) positioned on the housing 102 to interface with the computer 124 to lock or unlock the rear doors 602. The computer 124 may also be used to interface with the computer or computer network in the pharmacy to maintain an inventory of the prescription bags 212 in the unit 100. The computer 124 may further be used to interface with the computer or computer network in the pharmacy to access information specific to the customer, the customer's prescription, and/or the prescription bag 212.

The rear of the housing 102 may further include means to communicate with the technician or system operator to display whether the system is prepared to be accessed and reloaded. For example, lights 606 may be provided to communicate with the technician or operator, such as a red light may indicate that the machine is in operation and for the operator to wait to open the rear doors 602 or to pull out distribution trays 214 (see FIGS. 17 and 19). Further, a green light may signal to the technician or operator that the rear doors 602 may be opened and that distribution trays 214 may be removed from the unit 100 to be reloaded or inventoried.

When the unit 100 is idle, all of the platforms 216 may be moved to their lowest positions in the housing 102 so that bags 212 may not be removed from the distribution trays 214 without a distribution tray 214 being pulled out of the housing 102. In addition, the platforms 216 may be moved to their lowest positions in the housing 102 when the access door 313 or the rear doors 602 are opened. One or more tray sensors 576 (see FIG. 17) on the platforms 216 may signal the computer 124 and/or the controller 128 when a particular tray 214 is removed from a particular platform 216. If one or more trays 214 are removed from any of the platforms 216, those trays 214 that were removed are identified by the one or more tray sensors 576 so that only those removed trays 214 may be re-inventoried to determine or verify the contents of the trays 214. The inventory process as performed by the shuttle assembly 208 is discussed in greater detail below.

Figure 19:
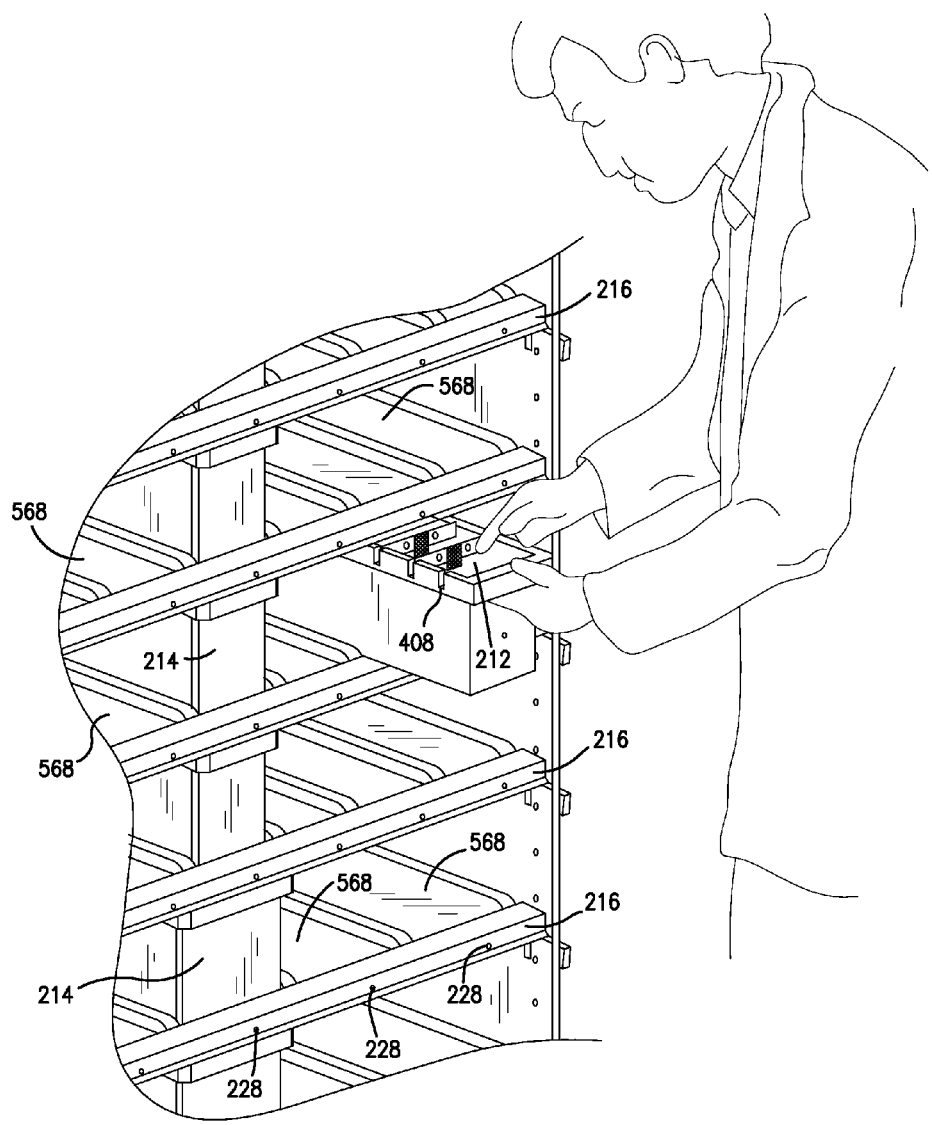
FIG. 19 is a rear perspective view of the dispensing unit of FIG. 1, illustrating the technician loading distribution trays into the dispensing unit.

As shown in FIG. 19, different sizes of trays 214 may be utilized in the unit 100. More particularly, the trays 214 may be configured in a standard size to receive prescription bags 212 of standard size, and a wide size to receive prescription bags 212 larger than the standard-sized bags 212. The platforms 216 may also be specifically configured to receive any of a number of different size trays 214, including the standard size and wide size trays 214. More particularly, the platforms 216 may include a plurality of guides 568, with each guide 568 being configured to receive one tray 214. The guides 568 may be permanently fixed (e.g., by welding, etc.) to the platforms 216 or releasably coupled (e.g., by fastening, using quick-release connectors, etc.) to the platforms 216. The platforms 216 and/or the guides 568 may be changed-out or re-configured on the installation site of the unit 100 to receive any of a number of different size trays 214.

Figure 18:
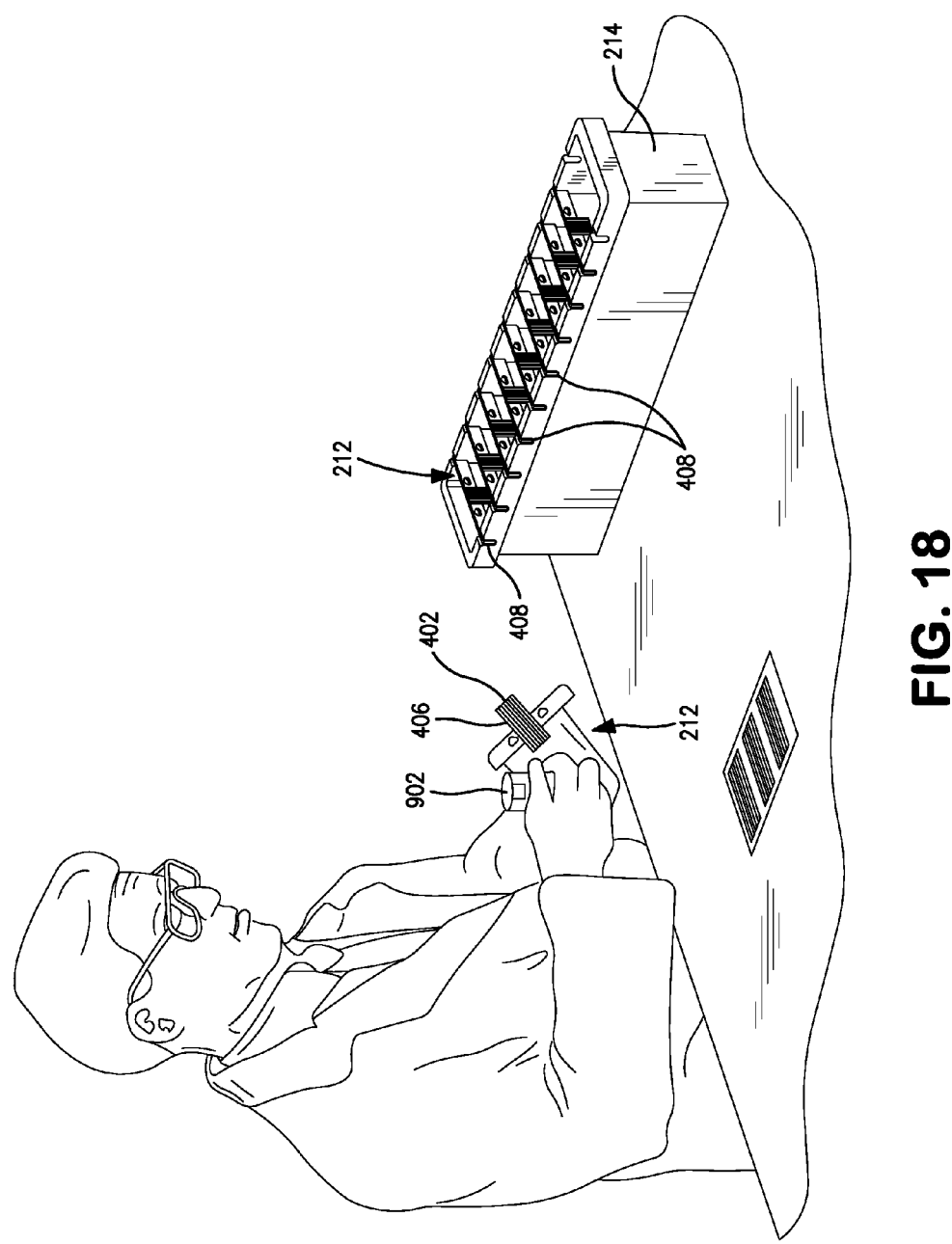
FIG. 18 is a perspective view of a technician/pharmacist loading the distribution trays with finished prescriptions.

FIG. 18 illustrates a pharmacist or technician filling prescriptions by placing a prescribed item 902 into the prescription bag 212. After placing the prescribed item 902 into the bag 212, the pharmacist or technician may close the bag 212 by removing the backing 528 and folding over the label 402 as described above. The pharmacist or technician may then use a barcode scanner (not shown) to scan the barcode 406 on the label 402 to match the prescribed item 902 and the prescription bag 212 to a customer in a database on the pharmacy's computer network.

The bag 212 may then be placed in any random location in the distribution tray 214 so that the bag 212 is captured between the pair of opposing notches 408. The pharmacist or technician may load the trays 214 with the prescription bags 212 at a remote location from the unit 100, such as a countertop in the pharmacy. The pharmacist or technician may access the rear of the housing 102 via the rear doors 602 and place the filled distribution tray 214 into an open guide 568. The pharmacist or technician may repeat this process as many times as necessary to place new prescription bags 212 into the unit 100 or to fill empty slots in the distribution trays 214.

The unit 100 may also include an auxiliary door (not shown) in one or both of the access door 313 and the rear doors 602 of sufficient size to allow a single tray 214 to be inserted or removed from the housing 102 without opening the access door 313 or the rear doors 602. Such an auxiliary door may allow reloading or restocking the unit 100 without taking the unit 100 off-line.

In addition, the unit 100 may utilize a hopper (not shown) to facilitate loading, reloading, or restocking the unit 100 with new prescription bags 212. For example, the pharmacist or technician may deposit the bags 212 in the hopper, and the shuttle assembly 208, alone or in combination with other components, may pick the bags 212 and load the bags 212 into a random location in the unit 100.

Figure 24:
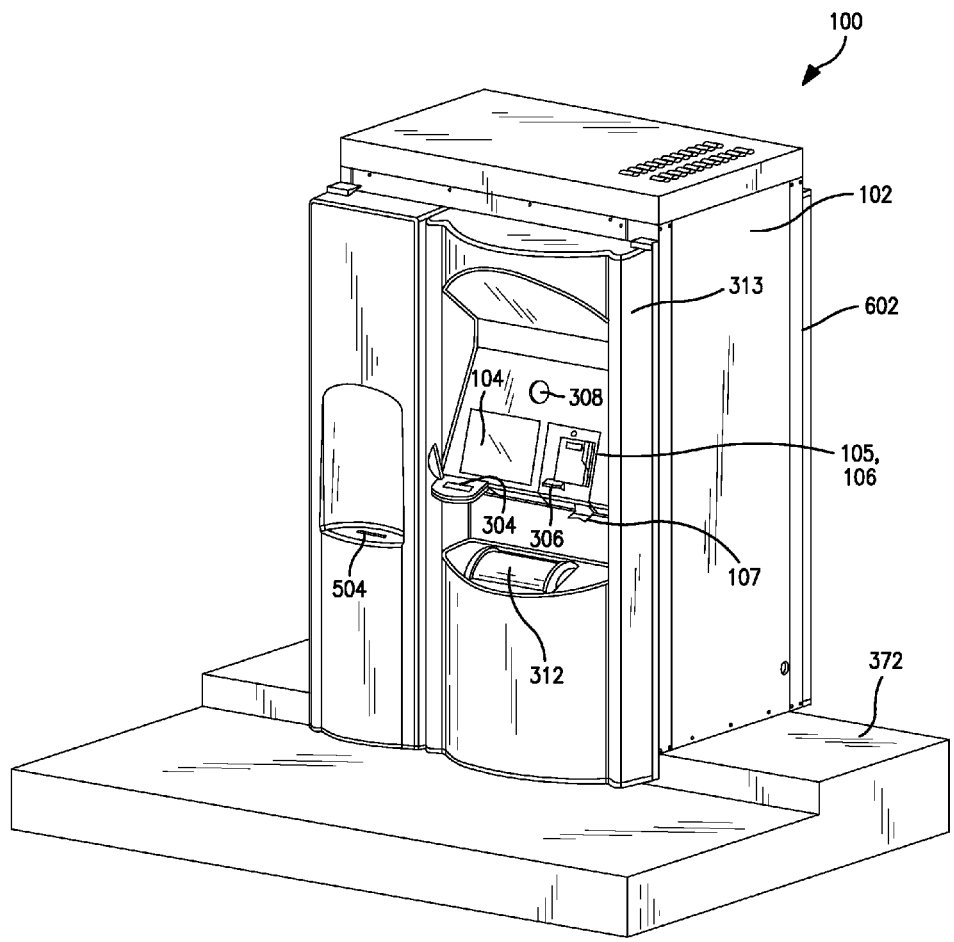
FIG. 24 is a front perspective view of the random access and random load dispensing unit of the present invention, illustrating a housing of the unit being vertically offset from an access door of the unit including customer interface components.

The unit 100 may be utilized at a location inside of a store, such as adjacent to a pharmacy counter. With reference to FIG. 24, the unit 100 may also be adjustable to account for pharmacies that are located on raised platforms 372. More particularly, the housing 102 of the unit 100 may be located on the same level as the pharmacist or technician who is standing on the raised platform 372, while the access door 313 including the customer interface components (i.e., the touch screen 104, magnetic stripe card reader 105 and/or credit card reader 106, barcode scanner 107, signature pad 304, receipt dispense opening 306, camera 308, and dispense bin 310) may be located at the same level as the customer, who is standing at a level or an elevation below the raised platform 372. This facilitates access into the housing 102 by the pharmacist or technician, while also facilitating access to the above-identified customer interface components by the customer. If a unit 100 were configured for use on a raised platform like that discussed above, the computer 124 may be configured appropriately to maneuver the shuttle assembly 208 in such a path to accommodate for the height difference between the dispense bin 310 and the housing 102.

The unit 100 may allow the customers to select, purchase, and receive their prescription drugs, or other consumer items effectively without human interaction in the store. More particularly, customers may purchase their prescription drugs without direct contact with the pharmacist or technician responsible for filing the customer's prescription. In such a capacity, the unit 100 effectively functions as an automated storage facility for storing prescription bags 212 in a location accessible to the customer, even during times when the store or pharmacy is closed. In addition, the unit 100 may be utilized outside of a store location, such as in an automobile drive-through system so that the customer may purchase their prescription bags 212 or other goods while remaining in their automobile.

Figure 25:
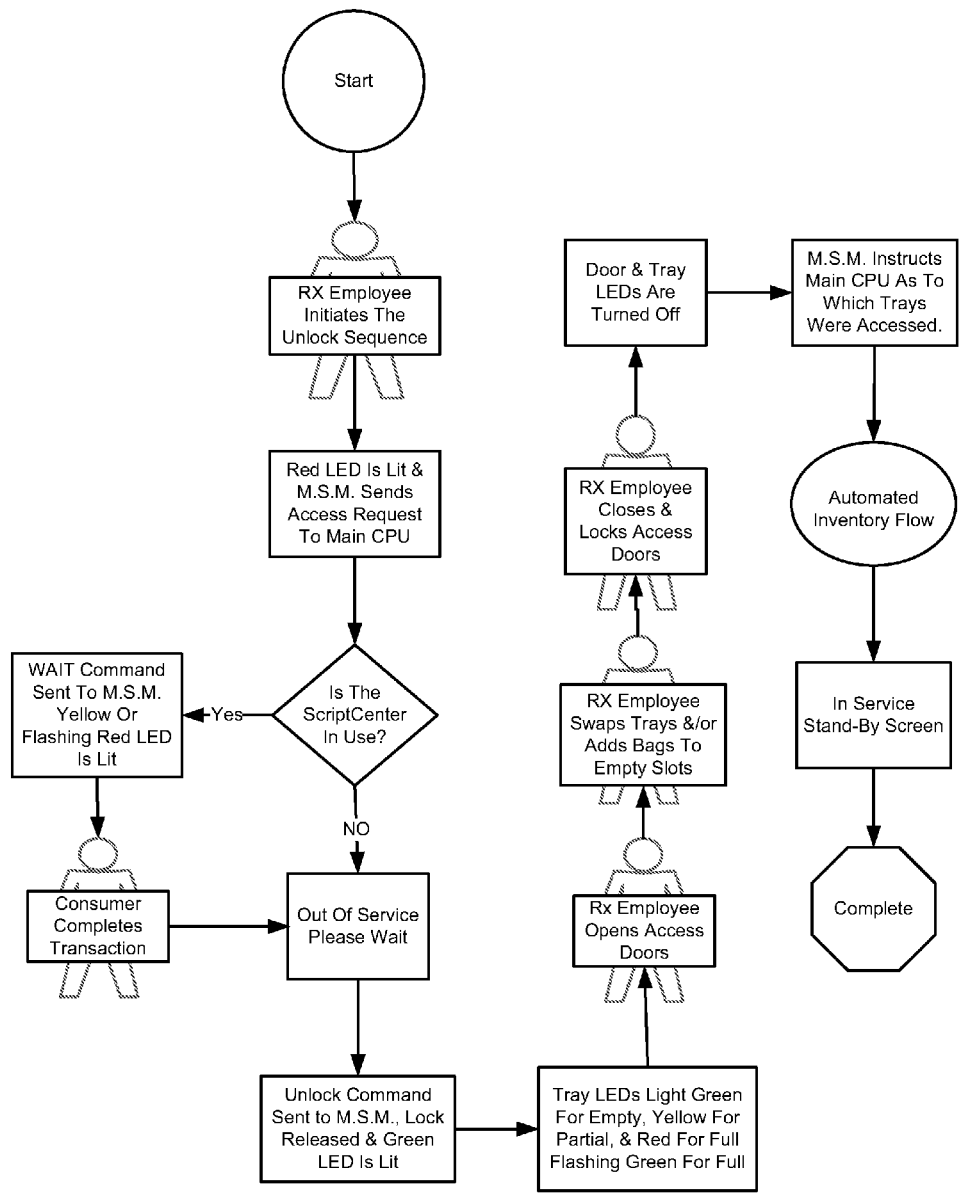
FIG. 25 is a flowchart schematically illustrating the loading process of the dispensing unit of FIG. 1.

With reference to FIG. 25, a process for loading the unit 100 is schematically illustrated. The loading process allows a pharmacist or a technician to replace empty trays 214 with filled trays 214 and/or fill empty slots in partially-empty trays 214 with new prescription bags 212 containing finished prescriptions.

In creating a finished prescription, as is customary, the pharmacist first receives a prescription for a customer from an authorized medical professional, selects an appropriate prescription drug to fill the customer's prescription, and then fills the container 902 with the selected prescription drug to fill the prescription. The pharmacist may then insert the container 902 into the prescription bag 212 and either transfer a label 402 including a barcode 406 from the prescription documentation to the bag 212 to identify the contents of the container 902 and/or the bag 212, or use a barcode reader to scan a pre-printed barcode on the bag 212 and then scan the barcode 406 associated with that prescription to correlate a particular bag 212 to a particular prescription in the database program of the computer 124. The pharmacist or technician may then insert the prescription bags 212 into one or more trays 214 for deposit into the unit 100, or the prescription bags 212 may be deposited into empty slots in partially-empty trays 214 during the loading process.

To load the unit 100, the pharmacist or technician may first initiate a sequence for unlocking the rear doors 602. During the sequence to unlock the rear doors 602, the controller 128 may interface with the computer 124 to request permission to unlock the rear doors 602. If the unit 100 is not in use by a customer, the touch screen 104 may display a message indicating the unit 100 is out of service, and the controller 128 receives a signal from the computer 124 to unlock the rear doors 602. After the rear doors 602 are unlocked, the pharmacist or technician may visually identify empty trays 214 and replace any empty trays 214 with filled trays 214 containing new prescription bags 212. The trays 214 may be removed and/or replaced in random locations in the unit 100. In other words, the trays 214 are not associated with permanent locations in the unit 100. The pharmacist or technician may also identify which trays are partially empty so that new prescription bags 212 may be inserted in the empty slots in the partially empty trays 214. The pharmacist or technician may identify which trays 214 are empty or partially empty by referencing indicator lights 228 (see FIG. 19) located adjacent or beneath the trays 214. The indicator lights 228 (e.g., bi-color LED's) may be varied between different colors and/or intensities (i.e., flashing) by the computer 124 and/or controller 128 to indicate various tray states or fill levels (e.g., a full tray 214, an empty tray 214, or a partially-empty tray 214). For example, the indicator lights 228 may flash green for a corresponding tray 214 containing bags 212 that should be removed due to passing of a pick-up date or an expiration date.

After the new prescription bags 212 have been deposited into the unit 100, the pharmacist or technician closes and locks the rear doors 602. The controller 128 may then interface with the computer 124 to relay which trays 214 were accessed by the pharmacist or technician in order to update the database program in the computer 124 to ascertain an accurate inventory of the prescription bags 212 in the unit 100. The updated inventory of prescription bags 212 in the unit 100 is performed by the shuttle assembly 208 passing over the new prescription bags 212 and reading their barcodes 406 with the barcode reader 210. To complete the loading process, the computer 124 may prompt the touch screen 104 to display a message indicating the unit 100 is back in service.

The unit 100 may also automatically consolidate partially-filled trays 214 without any input from the pharmacist or technician. For example, multiple partially-filled trays 214 may be identified while the shuttle assembly 208 re-inventories the bags 212 in the unit 100. The computer 124 and/or controller 128 may then re-assign the bags 212 in one of the partially-filled trays 214 to fill empty slots in other partially-filled trays 214. The controller 128 may then direct the shuttle assembly 208 to reposition the bags 212 accordingly. Prescription bags 212 containing expired filled prescriptions or expired products may be repositioned to a specific tray 214 for the pharmacist or technician to remove from the unit 100.

Figure 26:
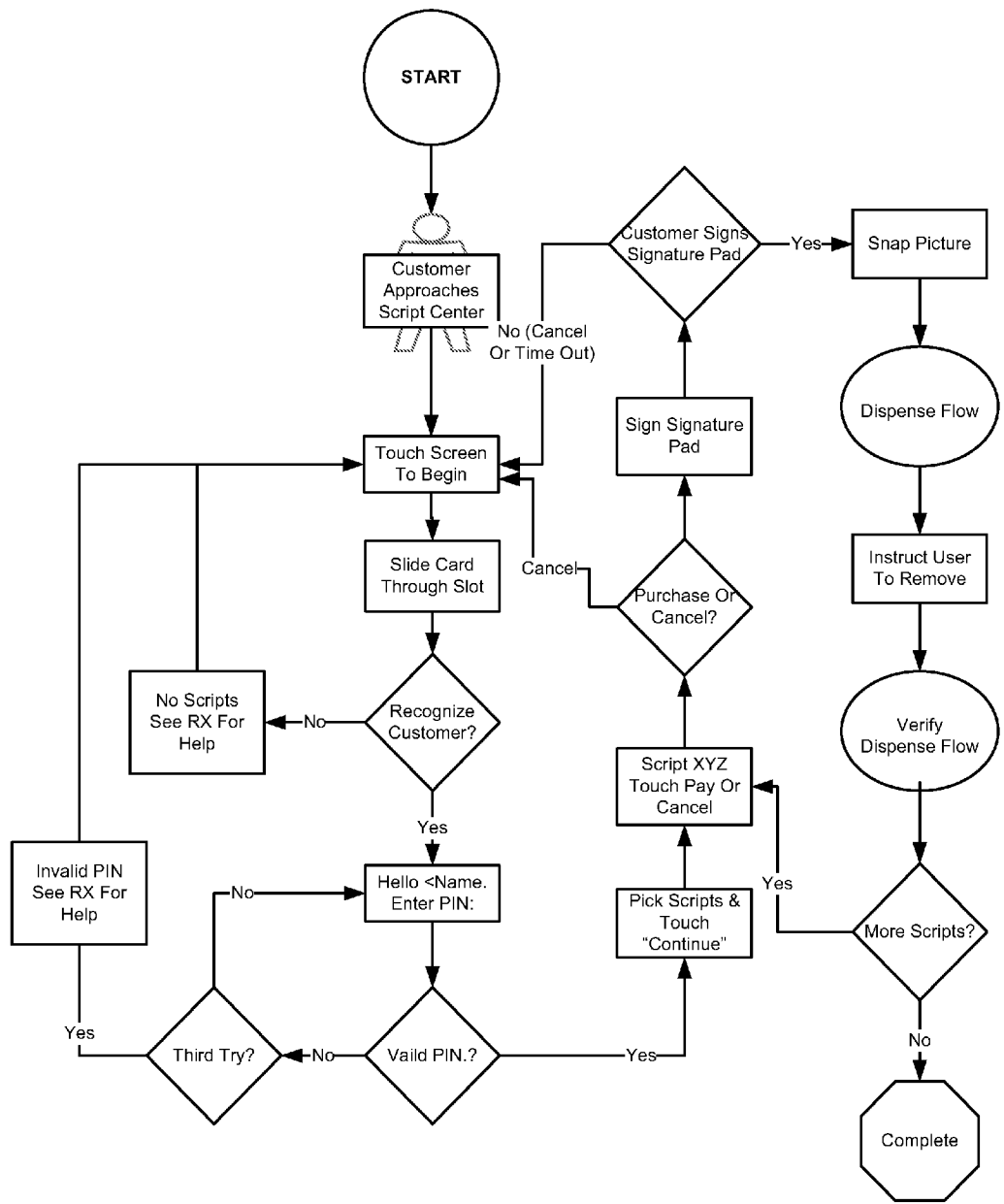
FIG. 26 is a flowchart schematically illustrating the dispensing process of the dispensing unit of FIG. 1.

With reference to FIG. 26, a process for dispensing the prescription bags 212 is schematically illustrated. The dispensing process may be initiated by a customer touching the touch screen 104, which may display a greeting message to the customer. Then, the customer may be instructed to identify themselves by, for example, sliding their credit card through an identification card reader (e.g., magnetic strip card reader 105 or credit card reader 106). The customer may also have their pharmacy discount card or prescription drug card scanned by the barcode scanner 107 for supplemental or primary identification purposes.

The database program in the computer 124 may then compare the customer's identity with the inventory of prescription bags 212 stored in the unit 100. If a prescription bag 212 corresponding to the customer is not found in the unit 100, the computer 124 may prompt the touch screen 104 to display a message referring the customer to the pharmacist or the technician for assistance. If a prescription bag 212 corresponding to the customer is found in the unit 100, the computer 124 may prompt the touch screen 104 to display a message displaying the customer's name and requesting the customer enter a password to verify their identity. Such a password may include a user-chosen password or a pre-assigned PIN that is stored locally in the database program of the computer 124 or remotely on another database program. If the customer enters an incorrect password or PIN, they may be re-directed back to the password-entry message one or more times before the computer 124 prompts the touch screen 104 to display a message instructing the customer of their invalid password or PIN. From this message, the computer 124 may prompt the touch screen 104 to return to the greeting message at the beginning of the dispensing process.

If the customer enters a password or PIN that is verified by the computer 124, the computer 124 may then query the database program to check the number of prescription bags 212 corresponding to the customer that are stored in the unit 100. The computer 124 may then prompt the touch screen 104 to display a message listing all of the prescription bags 212 corresponding to the customer that are stored in the unit 100. The customer may choose to purchase one, some, or all of the prescription bags 212 by touching/selecting each desired prescription displayed on the touch screen 104. Alternatively, if the customer logged in to the unit 100 utilizing the touch screen 104 rather than the credit card reader 106, the customer will be prompted through a payment selection process after selecting their desired prescriptions. Such a payment selection process can include being prompted to enter a credit card into the credit card reader 106 or entering cash into the cash acceptor.

If the customer chooses to continue with the transaction, the computer 124 may prompt the touch screen 104 to display a message instructing the customer to sign their name on a signature pad 304 to finalize their purchase of the selected prescriptions. The customer's signature is recorded electronically by the computer 124. If the customer chooses not to sign the signature pad 304, the computer 124 may prompt the touch screen 104 to return to the greeting message at the beginning of the dispensing process. However, if the customer signs the signature pad 304, the computer 124 may prompt the security camera 308 to photograph the customer to produce a photographic record of the transaction. Additionally, the customer's signature may be captured as required for third party insurance or MediCal transactions, acknowledgement of prescriptions that do not have a child restraint cap, or other regulatory information.

Figure 27:
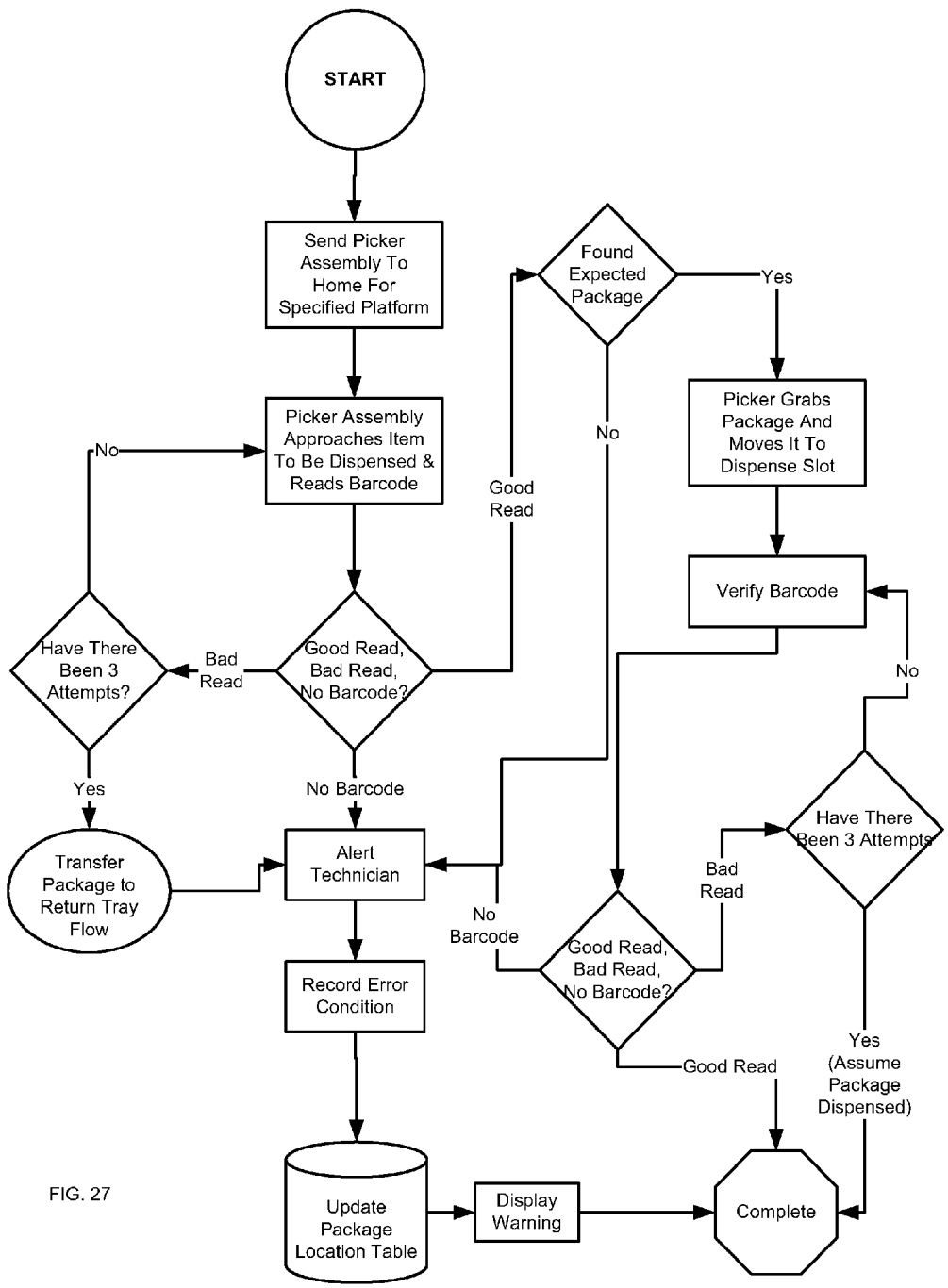
FIG. 27 is a flowchart schematically illustrating the operations performed by the dispensing unit of FIG. 1 in dispensing a finished prescription.

After taking the photograph, the computer 124 may interface with the controller 128 to provide instructions relating the location of the selected prescription bags 212. Further, the shuttle assembly 208 and the platforms 216 may be maneuvered as described above and in the flowchart illustrated in FIG. 27. After all of the selected prescription bags 212 are dispensed into the dispense bin 310, the computer 124 may prompt the touch screen 104 to display a message instructing the customer to remove the prescription bags 212 from the dispense bin 310. The computer 124 may then interface with the controller 128 and/or other sensors or components in the unit 100 to verify the dispensing of the prescription bags 212 and/or the recovery of the prescription bags 212 from the dispense bin 310.

Although the invention has been described in detail with reference to certain preferred embodiments, variations and modifications exist within the scope and spirit of the invention as described and defined in the following claims.

We claim:

1. A dispensing unit for storing and delivering items associated with a specific consumer comprising:
a housing that defines a first axis, a second axis, and a thirds axis, wherein the three axes are substantially perpendicular to one another;
a dispense location,
a computer;
a consumer interface device coupled to the housing and communicably coupled to the computer, and configured to receive consumer-identifying information;
a first plurality of three-dimensional storage locations intersected by a line parallel to the first axis, a second plurality of three-dimensional storage locations intersected by a line parallel to the second axis, and a third plurality of storage locations intersected by a line parallel to the third axis, wherein substantially all storage locations are configured to store at least one consumer-associated item that has been coupled with an electronically-readable identifying information for communicating that a stored item has been associated with a specific consumer;
a delivery assembly communicably coupled with the computer, and configured to move a consumer-associated item from a storage location to a dispense location;
an electronic information sensor communicably coupled with the computer, and configured to sense the electronically-readable identifying information and communicate at least the electronically-readable identifying information; and
wherein the computer receives the consumer-identifying information and the sensed electronically-readable identifying information to verify that electronically-readable information for the stored item matches the consumer-identifying information, and directs the delivery assembly to deliver the verified, consumer-associated item to the dispense point.

2. The dispensing unit of claim 1, wherein the consumer-associated item is a pharmacy-filled prescription.

3. The dispensing unit of claim 2, wherein the consumer interface comprises interface equipment selected from a group consisting of a touchscreen, a magnetic stripe card reader, a fingerprint reader, a retinal scanner, and a credit card reader.

4. The dispensing unit of claim 3, wherein the consumer interface device is configured to accept consumer identifying information.

5. The dispensing unit of claim 4, wherein the consumer identifying information comprises information selected from a group consisting of: a user name, a password, a prescription number, a product identifying number, a birth date, a social security number, a signature, and a personal identification number.

6. The dispensing unit of claim 3, wherein the information sensor senses the electronically-readable identifying information to associate a storage location and a consumer-specific item after being placed at the storage location.

7. The dispensing unit of claim 6, wherein the delivery assembly is configured to move a previously stored, consumer specific item from a first storage location to a second storage location within the dispensing unit and the dispensing unit is further configured to associate the consumer specific item to the second unique storage location.

8. The dispensing unit of claim 6, wherein the electronic information sensor is a barcode reader.

9. The dispensing unit of claim 8, wherein the electronic information sensor is coupled to the delivery assembly, and is translatable to every storage location.

10. The dispensing unit of claim 9, further comprising at least a first support located in the housing and extending along a first axis, a second support extending along a second axis, and a third support extending along a third axis, wherein the first, second, and third axes are substantially perpendicular to one another, and the delivery assembly is configured to move along the first axis, the second axis, and the third axis.

11. The dispensing unit of claim 10, wherein the delivery assembly further comprises a shuttle assembly, which is supported by the first support, and wherein the retrieving assembly further comprising a carriage movable along the second axis.

12. The dispensing unit of claim 11, wherein the carriage is movable along the third axis.

13. The dispensing unit of claim 12, wherein the shuttle assembly further comprises a picker assembly.

14. The dispensing unit of claim 13 wherein the electronically readable identifying information is located on a tag.

15. The dispensing unit of claim 14, wherein the tag comprises a bar-code.

16. The dispensing unit of claim 15, wherein the consumer associated items are placed within a container prior to being stored in the dispensing unit.

17. The dispensing unit of claim 16, wherein the container is a bag.

18. The dispensing unit of claim 17, wherein the electronically-readable identifying information is coupled to the bag.

19. The dispensing unit of claim 18, wherein the bag further comprises a header, and the electronically-readable identifying information is coupled to the header.

20. The dispensing unit of claim 1 further comprising a controller in communication with the computer and the delivery assembly.

21. The dispensing unit of claim 20, wherein the controller controls the delivery assembly and the electronic sensor.

22. The dispensing unit of claim 21, where in the storage location are movable by the controller along the first axis.

23. The dispensing unit of claim 22, further comprising a plurality of shelves for supporting the storage locations, wherein the controller controls the shelves to move to the storage locations along the first axis.

24. The dispensing unit of claim 1, wherein the computer is located remotely from the housing.

25. The dispensing unit of claim 1, further comprising a distribution bin for housing at least one of the plurality of storage locations.

26. The dispensing unit of claim 25, further comprising a plurality of distribution bins for housing substantially all of the plurality of storage locations.

27. The dispensing unit of claim 26, wherein the dispensing unit is located within a retail pharmacy store.

28. The dispensing unit of claim 26, wherein the distribution bins are removable from the dispenser.

29. The dispensing unit of claim 28, further comprising a plurality of movable shelves for supporting the plurality of distribution bins.

30. The dispensing unit of claim 28, wherein the distribution bin comprises a plurality of pairs of substantially aligned notches, each pair defining a storage location.

31. A dispensing unit for storing a plurality of finished prescriptions each having been associated with a specific consumer prior to storage, the dispensing unit comprising:
a housing defining an x axis, a y axis, and a z axis; the axes being substantially perpendicular to one another;
a user interface coupled to the housing and configured to receive consumer-identification information;
a plurality of storage locations extending along each of the x axis, the y axis, and the z axis wherein the plurality of storage locations form a three-dimensional matrix of storage locations, and wherein substantially all the storage locations are configured to store at least one finished prescription that has been coupled with electronically-readable information associating the finished prescription with a specific consumer prior to being placed within the dispensing unit;
a shuttle assembly movable along each of the x-axis, y-axis, and z-axis, configured to transport the finished prescription to a dispense point;
an electronic sensor, coupled to the shuttle assembly, and configured to sense the electronically-readable information from the storage locations;
a computer in communication with the user interface and a controller,
wherein the computer is configured to receive the consumer-identification information and request delivery of a stored finished prescription, and the controller is configured to (1) direct the shuttle assembly to move to a storage location where the finished prescription is stored, (2) direct the electronic reader to send electronic information obtained from the electronically-readable information to the computer to allow for verification that the stored prescription has been filled for the consumer associated with the consumer-identification information and is the finished prescription requested for delivery, and (3) cause the shuttle assembly to deliver the finished prescription to the dispense point.

* * * * *